(12) United States Patent
Walters et al.

(10) Patent No.: US 11,618,756 B2
(45) Date of Patent: Apr. 4, 2023

(54) COMPOUNDS FOR COORDINATING WITH A METAL, COMPOSITIONS CONTAINING SUCH COMPOUNDS, AND METHODS OF CATALYZING REACTIONS

(71) Applicant: PPG Industries Ohio, Inc., Cleveland, OH (US)

(72) Inventors: Robert W. Walters, Murrysville, PA (US); Scott J. Moravek, Mars, PA (US); Sujit Mondal, Gibsonia, PA (US); Ian Michael Jones, Pittsburgh, PA (US); Anthony T. Gestrich, Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 16/979,413

(22) PCT Filed: Mar. 11, 2019

(86) PCT No.: PCT/US2019/021665
§ 371 (c)(1),
(2) Date: Sep. 9, 2020

(87) PCT Pub. No.: WO2019/173836
PCT Pub. Date: Sep. 12, 2019

(65) Prior Publication Data
US 2021/0079009 A1 Mar. 18, 2021

Related U.S. Application Data

(60) Provisional application No. 62/640,703, filed on Mar. 9, 2018.

(51) Int. Cl.
| | | |
|---|---|---|
| *C07D 491/20* | (2006.01) | |
| *C08G 18/22* | (2006.01) | |
| *C08G 18/24* | (2006.01) | |
| *C08G 18/62* | (2006.01) | |
| *C08G 18/79* | (2006.01) | |
| *C09D 175/16* | (2006.01) | |

(52) U.S. Cl.
CPC ......... *C07D 491/20* (2013.01); *C08G 18/222* (2013.01); *C08G 18/242* (2013.01); *C08G 18/6229* (2013.01); *C08G 18/792* (2013.01); *C09D 175/16* (2013.01)

(58) Field of Classification Search
None
See application file for complete search history.

(56) References Cited

U.S. PATENT DOCUMENTS

| | | |
|---|---|---|
| 6,458,885 B1 | 10/2002 | Stengel et al. |
| 8,318,830 B2 | 11/2012 | Kohli Steck et al. |
| 9,617,365 B2 | 4/2017 | Moravek et al. |
| 2004/0234698 A1 | 11/2004 | Wilt et al. |
| 2004/0259975 A1 | 12/2004 | Robillard |
| 2012/0259033 A1 | 10/2012 | Hintermann et al. |

FOREIGN PATENT DOCUMENTS

| | | |
|---|---|---|
| EP | 1038870 A1 | 9/2000 |
| WO | 2017087055 A1 | 5/2017 |

OTHER PUBLICATIONS

Rich et al. N-Tetradentate SPANamine Derivatives and Their MnII-Complexes as Catalysts for Epoxidation of Alkenes. European Journal of Inorganic Chemistry (2013), (7), 1213-1224 (Year: 2013).*
Sala et al. Modular spiro bidentate nitrogen ligands—synthesis, resolution and application in asymmetric catalysis. European Journal of Organic Chemistry (2008), (36), 6197-6205. (Year: 2008).*
Jacquet et al. SPANphos Ligands in Palladium-Catalyzed Asymmetric Fluorination. European Journal of Organic Chemistry, 2012 (25), 4844-4852 (Year: 2012).*
Diebolt et al. Strong π-Acceptor Ligands in Rhodium-Catalyzed Hydroformylation of Ethene and 1-Octene: Operando Catalysis. ACS Catalysis (2013), 3(2), 128-137 (Year: 2013).*
Chernyshev et al., "Metal complexes of new photochromic chelator: Structure, stability and photodissociation", Journal of Photochemistry and Photobiology A: Chemistry, 2013, vol. 265, pp. 1-9.
Collados et al., "Microwave-Assisted Solvent-Free Synthesis of Enantiomerically Pure N-(tert-Butylsulfinyl)imines", The Journal of Organic Chemistry, 2012, vol. 77, pp. 5744-5750.
Collins et al., "Photoinduced switching of metal complexation by quinolinospiropyranindolines in polar solvents", Chem. Commun., 1999, pp. 321-322.
Matsumoto et al., "Rapid, Low Temperature Formation of Imine-Linked Covalent Organic Frameworks Catalyzed by Metal Triflates", Journal of the American Chemical Society, 2017, vol. 139, pp. 4999-5002.
Phillips et al., "Photochromic Chelating Agents", Journal of the American Chemical Society, 1965, vol. 87:17, p. 4020.
Winkler et al., "Photodynamic Fluorescent Metal Ion Sensors with Parts per Billion Sensitivity", Journal of the American Chemical Society, 1998, vol. 120, pp. 3237-3242.

* cited by examiner

*Primary Examiner* — Sanza L. McClendon

(57) ABSTRACT

A compound capable of coordinating with a metal includes a chemical structure as shown in claim 1, in which: EPD represents a group having an electron pair donor atom; B and B' are each independently an aryl group, a heteroaryl group, an alkenyl group, or alkynyl group, or B and B' form a spirocyclic group; and $R_1$, $R_2$, and $R_3$ are selected from various substituents.

20 Claims, 1 Drawing Sheet

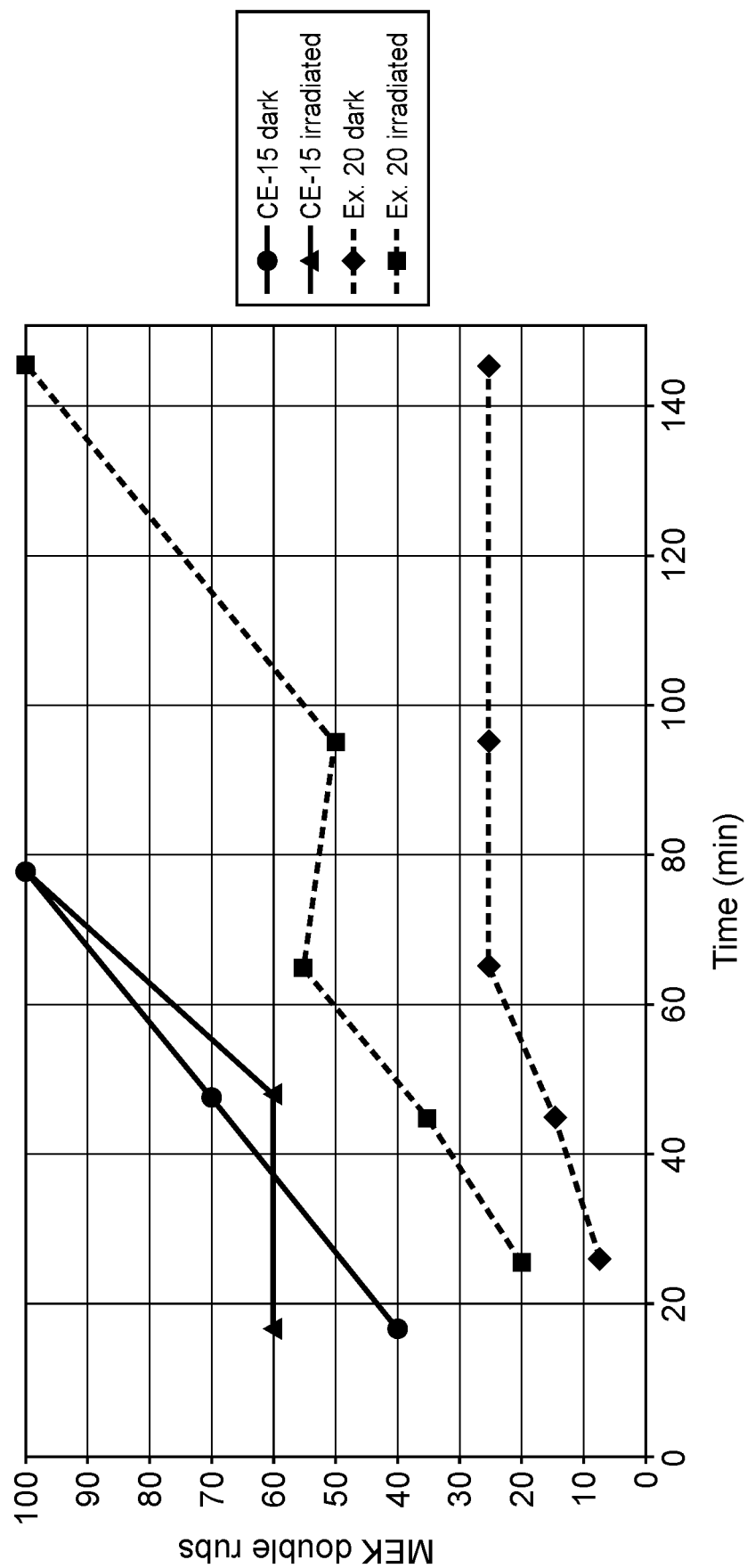

COMPOUNDS FOR COORDINATING WITH A METAL, COMPOSITIONS CONTAINING SUCH COMPOUNDS, AND METHODS OF CATALYZING REACTIONS

FIELD OF THE INVENTION

The present invention relates to compositions that include latent catalysts and methods of catalyzing reactions using latent catalysts.

BACKGROUND OF THE INVENTION

Catalysts are commonly added to compositions to initiate or increase the rate of reaction between reactive materials that form a portion of such compositions. For example, coating compositions often contain a catalyst that helps increase the reaction rate between one or more reactive materials that form at least a portion of the binder of the final coating. However, while such catalysts help increase the reaction rate between the reactive materials, they also decrease the pot life of the composition, which is the period of time the mixed composition remains stable and suitable for its intended use, for example, as a coating. It is therefore desirable to provide coating compositions with catalysts that increase the reaction rate between one or more reactive materials that form at least a portion of the composition, and which also provide an extended pot life before application.

SUMMARY OF THE INVENTION

The present invention relates to a compound capable of coordinating with a metal comprising a chemical structure represented by Formula (II)-B,

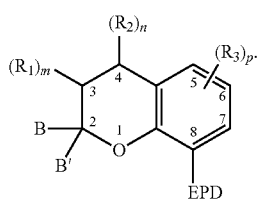

Formula (II)-B

As to Formula (II)-B, EPD represents a group comprising an electron pair donor atom; B and B' are each independently an aryl group, a heteroaryl group, an alkenyl group, or alkynyl group, or B and B' taken together form a spirocyclic group; $R_1$ and $R_2$ each independently comprise a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, a spirocyclic group, or any combination thereof, or $R_1$ and $R_2$ together form a cycloalkyl group or a heterocyclic group; and m and n are each independently a number selected from 0 to 2. Further, each $R_3$ independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof; and p is a number selected from 0 to 3.

The present invention also relates to a composition comprising: a) a reactive material comprising at least one of: i) one or more cationic polymerizable components; and ii) an active hydrogen functional first component, and a second component reactive with the active hydrogen groups of the first component; and b) a latent catalyst. The latent catalyst comprises a reaction product formed from components comprising: a ligand; and a metal compound sufficient to catalyze the reactive material. Further, the ligand is derived from a compound represented by the following Formula (I)-B,

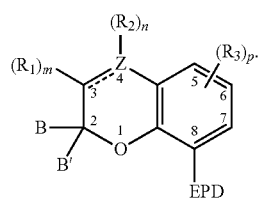

Formula (I)-B

As to Formula (I)-B, EPD represents a group comprising an electron pair donor atom; Z comprises carbon or nitrogen; B and B' are each independently an aryl group, a heteroaryl group, an alkenyl group, or alkynyl group, or B and B' taken together form a spirocyclic group; $R_1$ and $R_2$ each independently comprise a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, a spirocyclic group, or any combination thereof, or $R_1$ and $R_2$ together form a cycloalkyl group, a heterocyclic group, an aromatic, or a heteroaromatic group; a bond between positions 3 and 4 is a single bond or a double bond, with the proviso that Z is carbon when the bond between positions 3 and 4 is a single bond; and m and n are each independently a number selected from 0 to 2. Further, each $R_3$ independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof; and p is a number selected from 0 to 3.

The present invention also relates to a method of catalyzing a reaction comprising irradiating a composition comprising: a) a reactive material comprising at least one of: i) one or more cationic polymerizable components; and ii) an active hydrogen functional first component, and a second component reactive with the active hydrogen groups of the first component; and b) a latent catalyst. The latent catalyst comprises a reaction product formed from components comprising: a ligand; and a metal compound sufficient to catalyze the reactive material. Further, the ligand is derived from a compound represented by the following Formula (I)-B,

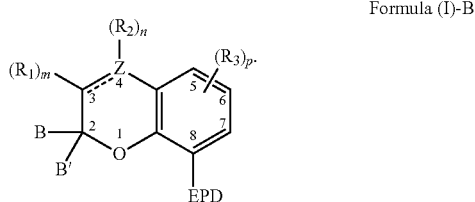

Formula (I)-B

As to Formula (I)-B, EPD represents a group comprising an electron pair donor atom; Z comprises carbon or nitrogen; B and B' are each independently an aryl group, a heteroaryl group, an alkenyl group, or alkynyl group, or B and B' taken together form a spirocyclic group; $R_1$ and $R_2$ each independently comprise a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, a spirocyclic group, or any combination thereof, or $R_1$ and $R_2$ together form a cycloalkyl group, a heterocyclic group, an aromatic, or a heteroaromatic group; a bond between positions 3 and 4 is a single bond or a double bond, with the proviso that Z is carbon when the bond between positions 3 and 4 is a single bond; and m and n are each independently a number selected from 0 to 2. The composition is irradiated with actinic radiation such that the ligand is disassociated from the reaction product. Further, each $R_3$ independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof; and p is a number selected from 0 to 3.

BRIEF DESCRIPTION OF THE DRAWINGS

FIG. 1 illustrates a graph of methyl ethyl ketone (MEK) double rub cure profiles of coatings formed from pigmented compositions.

DESCRIPTION OF THE INVENTION

For purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

In this application, the use of the singular includes the plural and plural encompasses singular, unless specifically stated otherwise. In addition, in this application, the use of "or" means "and/or" unless specifically stated otherwise, even though "and/or" may be explicitly used in certain instances. Further, in this application, the use of "a" or "an" means "at least one" unless specifically stated otherwise. For example, "a" reactive material, "a" latent catalyst, "a" ligand, and the like refer to one or more of any of these items.

As used herein, an "aryl group" refers to an aromatic cyclic monovalent hydrocarbon radical, and the term "aromatic" refers to a cyclically conjugated hydrocarbon with a stability (due to delocalization) that is significantly greater than that of a hypothetical localized structure. The aryl group may include, but is not limited to, a cyclic $C_3$-$C_{19}$ aromatic monovalent hydrocarbon radical, or an aromatic cyclic $C_3$-$C_{12}$ monovalent hydrocarbon radical, or an aromatic cyclic $C_6$-$C_{10}$ monovalent hydrocarbon radical. Non-limiting examples of aryl groups include, but are not limited to, phenyl, naphthyl, phenanthryl, and anthracenyl.

Further, a "heteroaryl group" refers to an aryl group, as previously described, in which at least one heteroatom (such as nitrogen, oxygen, or sulfur) is in the aromatic ring, or in at least one aromatic ring in the case of a fused ring polycyclic heteroaryl group. Non-limiting examples of heteroaryl groups include, but are not limited to, triazyl, furanyl, pyranyl, pyridinyl, isoquinoline, and pyrimidinyl.

An "alkenyl group" refers to a linear or branched monovalent hydrocarbon radical comprising one or more double bonds. The alkenyl group may include, but is not limited to, a linear or branched $C_1$-$C_{30}$ monovalent hydrocarbon radical comprising one or more double bonds, or a linear or branched $C_1$-$C_{20}$ monovalent hydrocarbon radical comprising one or more double bonds, or a linear or branched $C_1$-$C_{10}$ monovalent hydrocarbon radical comprising one or more double bonds, or a linear or branched $C_1$-$C_6$ monovalent hydrocarbon radical comprising one or more double bonds, or a linear or branched $C_2$-$C_4$ monovalent hydrocarbon radical comprising one or more double bonds.

An "alkynyl group" refers to a linear or branched monovalent hydrocarbon radical comprising one or more triple bonds. The alkynyl group may include, but is not limited to, a linear or branched $C_1$-$C_{30}$ monovalent hydrocarbon radical comprising one or more triple bonds, or a linear or branched $C_1$-$C_{20}$ monovalent hydrocarbon radical comprising one or more triple bonds, or a linear or branched $C_1$-$C_{10}$ monovalent hydrocarbon radical comprising one or more triple bonds, or a linear or branched $C_1$-$C_6$ monovalent hydrocarbon radical comprising one or more triple bonds, or a linear or branched $C_2$-$C_4$ monovalent hydrocarbon radical comprising one or more triple bonds.

A "spirocyclic group" refers to a twisted structure of two or more cyclic rings in which at least two of the rings are linked together by one common atom.

The term "linear" refers to a compound having a straight hydrocarbon chain, the term "branched" refers to a compound having a hydrocarbon chain with a hydrogen replaced by a sub stituent such as an alkyl group that branches or extends out from a straight chain, and the term "cyclic" refers to a closed ring structure. The cyclic groups also encompass bridged ring polycycloalkyl groups (or bridged ring polycyclic groups) and fused ring polycycloalkyl groups (or fused ring polycyclic groups).

As previously described, the present invention relates to a compound capable of coordinating with a metal. The compound can comprise a polycyclic compound that has a closed state and an open state. In the open state, the compound forms a chelate with a metal compound. As used herein, a "chelate" refers to a compound containing a ligand (typically organic) bonded to a central metal atom at two or more points.

The compound can comprise a photoactive compound. A "photoactive compound" refers to a compound that undergoes a conformational change in response to the absorption of actinic radiation. As used herein, "actinic radiation" refers to electromagnetic radiation that can initiate chemical reactions. Actinic radiation includes, but is not limited to, visible light, ultraviolet (UV) light, infrared and near-infrared radiation, X-ray, and gamma radiation.

The compound capable of coordinating with a metal can comprise a chemical structure represented by the following Formula (I):

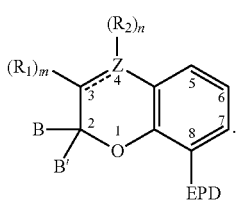

Formula (I)

With respect to Formula (I), EPD represents a group comprising an electron pair donor atom and Z comprises carbon or nitrogen. As used herein, an "electron pair donor atom" refers to an atom that donates electrons to another atom to form an electron donor-acceptor bond. The electron pair donor atom used with the present invention can comprise a nitrogen atom, an oxygen atom, a phosphorus atom, or a carbene. Non-limiting examples of a group comprising an electron pair donor atom includes a cyclic ring comprising at least one of a nitrogen atom, an oxygen atom, and/or a phosphorus atom. Further, the electron pair donor atom on the EPD is situated so that a 5- or 6-membered chelate can be formed with a metal, such as with the electron pair donor atom and the atom at position 1 of Formula (I) for example.

Referring to Formula (I), B and B' each independently comprise an aryl group, a heteroaryl group, an alkenyl group, or an alkynyl group, or B and B' taken together, such as with an intervening carbon atom, form a spirocyclic group. The spirocyclic group can comprise a nitrogen, an oxygen, or a sulfur atom such as, for example, a nitrogen, an oxygen, or a sulfur atom directly bonded to the 2-position. For example, B and B' can each independently comprise an aryl group, or can be taken together to form a spirocyclic group comprising a nitrogen, an oxygen, or a sulfur atom. Non-limiting examples of such rings include dihydrothiophene, dihydropyrrole, dihydrofuran, indoline, 2,3-dihydrobenzothiophene, 2,3-dihydrobenzofuran), and 2,3-dihydrobenzo[d]thiazole.

Referring again to Formula (I), $R_1$ and $R_2$ each independently comprise a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, a spirocyclic group, or any combination thereof. For example, $R_1$ and $R_2$ can each independently comprise an alkyl group, an aryl group, a halo group, an alkenyl group, or an alkynyl group. Additionally, $R_1$ and $R_2$ can together form a cycloalkyl group, a heterocyclic group, an aromatic, or a heteroaromatic group.

It is appreciated that a bond between positions 3 and 4 of Formula (I) can be a single bond or a double bond, with the proviso that Z is carbon when the bond between positions 3 and 4 is a single bond. Further, with respect to Formula (I), m and n are each independently a number selected from 0 to 2.

It is further appreciated that m and n will vary based on the bond between positions 3 and 4 and whether Z is carbon or nitrogen. For instance, when the bond between positions 3 and 4 is a single bond and Z is carbon, then m and n are each independently a number selected from 0 to 2. Further, when the bond between positions 3 and 4 is a double bond and Z is carbon, then m and n are each independently a number selected from 0 to 1. Alternatively, when the bond between positions 3 and 4 is a double bond and Z is nitrogen, then m is a number selected from 0 to 1 and n is 0.

Further, various substituents can present and associated with each carbon atom located at positions 5-7 of Formula (I). Non-limiting examples of suitable substituents include a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof. The substituent of a carbon atom at one of positions 5-7 can also form a fused ring with a substituent of an adjacent carbon atom, such as the EPD of the carbon at position 8 or a substituent of a carbon at locations 5, 6, or 7. It is appreciated that additional functionalities may be present remote from the core structure in Figure (I) provided that they do not interfere with the reaction between the compound of Formula (I) and a metal compound.

The previously described substituents of the carbon atoms located at positions 5-7 can be represented by the following Formula (I)-B,

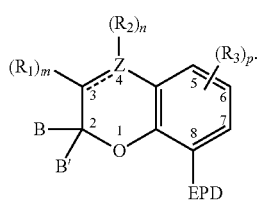

Formula (I)-B

As to Formula (I)-B, each $R_3$ independently comprises any of the previously described substituents of the carbon atoms located at positions 5-7, and p is a number selected from 0 to 3.

The compound can also comprise a chemical structure according to Formula (II), which is derived from Formula (I):

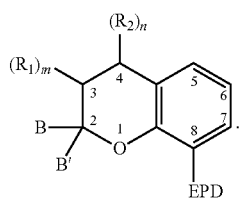

Formula (II)

It is appreciated that the EPD, $R_1$, $R_2$, B, and B' of Formula (II) are selected from any of the substituents previously described with respect to Formula (I). With respect to Formula (II), m and n are each independently a number selected from 0 to 2.

The compound comprising the chemical structure represented by Formula (II) can also comprise any of the previously described substituents of the carbon atoms located at positions 5-7. The previously described substituents of the carbon atoms located at positions 5-7 can be represented by the following Formula (II)-B,

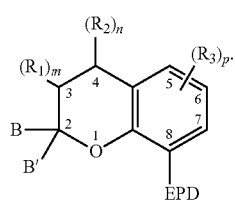

Formula (II)-B

As to Formula (II)-B, each $R_3$ independently comprises any of the previously described substituents of the carbon atoms located at positions 5-7, and p is a number selected from 0 to 3.

The ligand can also comprise a compound according to Formula (III), which is derived from Formulas (I) and (II):

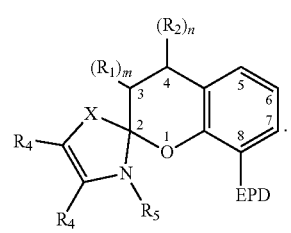

Formula (III)

It is appreciated that the EPD, $R_1$, and $R_2$ of Formula (III) are selected from any of the substituents previously described with respect to Formula (I). Further, m and n are each independently a number selected from 0 to 2, and each $R_4$ is a hydrogen or each $R_4$ together forms a fused aryl ring. $R_5$ is a hydrogen or alkyl group. X is $C(Me)_2$, O, N—$R_5$, or S in which Me is a methyl group. In some examples, $R_2$ comprises an alkenyl group substituted with B and B' previously described.

The compound comprising the chemical structure represented by Formula (III) can also comprise any of the previously described substituents of the carbon atoms located at positions 5-7. The previously described substituents of the carbon atoms located at positions 5-7 can be represented by the following Formula (III)-B,

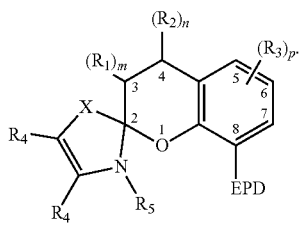

Formula (III)-B

As to Formula (III)-B, in which each $R_3$ independently comprises any of the previously described substituents of the carbon atoms located at positions 5-7, and p is a number selected from 0 to 3.

The compound can also comprise at least one chemical structure represented by at least one of Formula (IV), Formula (V), Formula (VI), and Formula (VII), which are derived from Formulas (I) and (II):

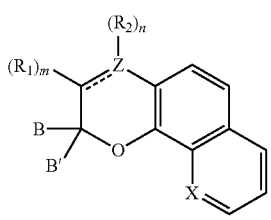

Formula (IV)

-continued

Formula (V)

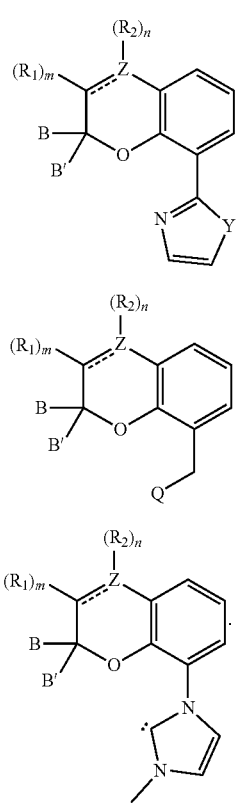

Formula (VI)

Formula (VII)

With respect to Formulas (IV)-(VII), Z comprises carbon or nitrogen; X is nitrogen or C—OH; Y is oxygen, sulfur, N—CH$_3$ or —CH=CH—; and Q comprises an amine or a phosphine. It is appreciated that R$_1$ and R$_2$ are selected from any of the substituents previously described with respect to Formula (I).

Non-limiting examples of more specific compounds derived from the above Formulas include, but are not limited to, the following structures:

Structure (I)

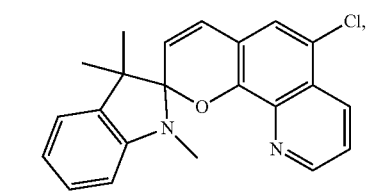

Structure (II)

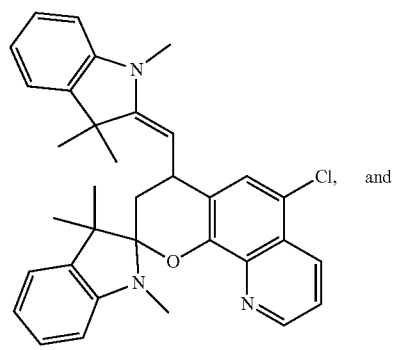

-continued

Structure (III)

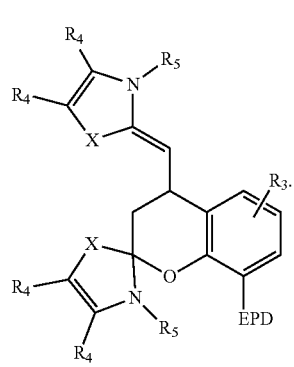

It is appreciated that the EPD, R$_1$, R$_2$, R$_3$ R$_4$, and R$_5$ of Structure (III) are selected from any of the substituents previously described with respect to the above Formulas. It is also understood that undesignated valencies in any of the previously formulas and structures are occupied by a hydrogen.

Other non-limiting examples of structures formed from the previously described formulas include the following and which also represent examples of various appropriate EPD groups:

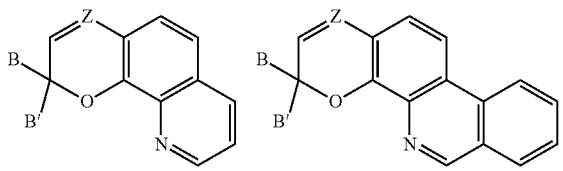

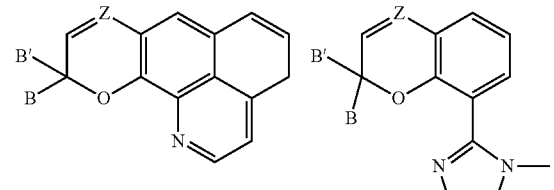

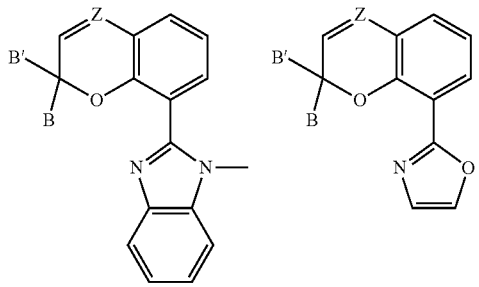

-continued

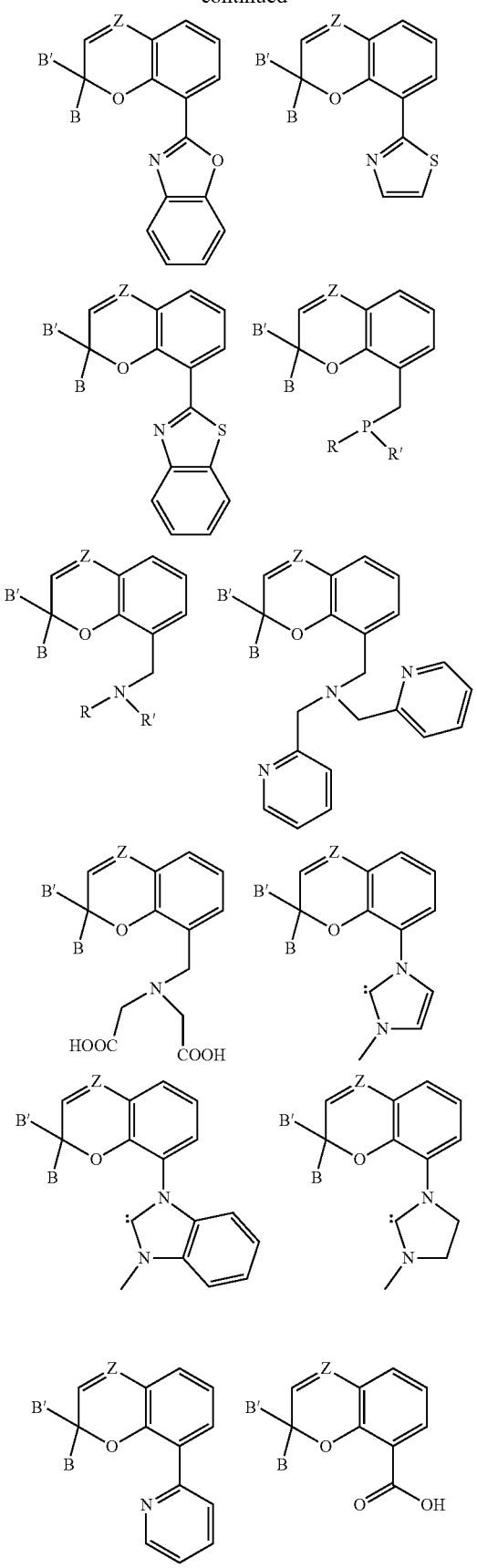

With respect to the above structures, Z, B, and B' are selected from any of the substituents previously described with respect to Formula (I), and R and R' are $C_1$-$C_{20}$ alkyl or phenyl groups. Although not depicted with a dashed line, it is appreciated that the bond between positions 3 and 4 can be a single bond or a double bond as in Formula (I), with the proviso that Z is carbon when the bond between positions 3 and 4 is a single bond.

As indicated, the previously described compounds are capable of coordinating with a metal. The present invention therefore also includes a chelate comprising the reaction product of the previously described compound and a metal compound.

The present invention also relates to a composition comprising: a) a reactive material; and b) a latent catalyst. As used herein, a "reactive material" refers to one or more types of components that are reactive with each other or are self-reactive and react with itself. In accordance with the present invention, the reactive component is selected from at least one of: i) one or more cationic polymerizable components; and ii) an active hydrogen functional first component and a second component reactive with the active hydrogen groups of the first component.

As used herein, a "cationic polymerizable component" refers to a component such as a monomer capable of undergoing a cationic atom polymerization reaction that involves addition of a double bond to a cationic center. Non-limiting examples of suitable cationic polymerizable components include vinyl compounds, cyclic ether compounds, cyclic thioether compounds, cyclic amine compounds, and combinations thereof. A "vinyl compound" refers to a compound that includes a terminal carbon-carbon double bond. Non-limiting examples of vinyl compounds include allyl functional compounds, (meth)acrylate functional compounds, styrene based compounds, and any combination thereof. The term "(meth)acrylate" refers to both the acrylate and the methacrylate. The cationic polymerizable component can include one type of component that reacts with itself (i.e., self-reactive) or multiple types of components that react with each other and/or themselves.

Further, and as indicated above, the reactive material can comprise an active hydrogen functional first component and a second component reactive with the active hydrogen groups of the first component. It is appreciated that the resulting reaction can form a polymer. An "active hydrogen functional component" refers to a compound that comprises one or more, typically at least two, functional groups having a hydrogen that displays activity according to the Zerewitinoff test. Accordingly, active hydrogens include hydrogen atoms attached to oxygen, nitrogen, or sulfur. Non-limiting examples of active hydrogen functional groups include hydroxyl groups, thiol groups, primary amine groups, secondary amine groups, carboxylic acid groups, carboxamide groups, or any combination thereof. The active hydrogen functional group can also include hydrazide groups.

The second component is selected based on the active hydrogen functional groups of the first component such that the second component reacts with the first component to form a desired reaction product. For example, the second component can comprise one or more, typically at least two, isocyanate groups, isothiocyanate groups, alkoxysilane groups, activated double bonds such as α,β-unsaturated carbonyls and α,β-unsaturated nitriles, epoxide groups, episulfide groups, aziridine groups, or any combination thereof. It is appreciated that such groups are reacted with the first component that comprises hydroxyl groups, thiol groups, amine groups, carboxylic acid groups, carboxamide groups, or any combination thereof to form a desired reaction product. For instance, the first component and second component can be selected to provide: an addition reaction such as a reaction between a first component comprising active hydrogen groups and a second component comprising isocyanate groups, isothiocyanate groups, α,β-unsaturated carbonyls, or α,β-unsaturated nitriles; a ring opening reaction such as a reaction between a first component comprising active hydrogen groups and a second component comprising epoxy groups, aziridine groups, and/or episulfide groups; or a condensation reaction such as a reaction between a first component comprising active hydrogen groups and a second component comprising an alkoxysilane group.

In another non-limiting example, the second component comprises one or more, typically at least two, ketone groups, aldehyde groups, or combinations thereof. It is appreciated that such groups are reacted with a first component that comprises one or more hydrazide groups, amine groups, or combinations thereof.

The previously described active hydrogen functional components and the components reactive with the active hydrogen functional components can each independently comprise monomers, polymers, or a combination thereof. As used herein, a "polymer" refers to oligomers and homopolymers (e.g., prepared from a single monomer species), copolymers (e.g., prepared from at least two monomer species), and graft polymers. The term "resin" is used interchangeably with the term "polymer."

Further, the active hydrogen functional first component can comprise one or more, such as at least two, active hydrogen functional groups. Similarly, the second component can comprise one or more, such as at least two, functional groups that are reactive with the active hydrogen functional groups. Any combination of the above first components and second components can be used as the reactive material.

The reactive material can comprise at least 10 weight %, such as at least 30 weight %, or at least 40 weight %, or at least 50 weight % of the composition, based on the total solids weight of the composition. The reactive material can comprise up to 99.99 weight %, such as up to 95 weight %, or up to 90 weight %, or up to 80 weight %, or up to 70 weight % of the composition, based on the total solids weight of the composition.

As indicated, the composition also comprises a latent catalyst. As used herein, a "latent catalyst" refers to a compound that when irradiated with actinic radiation produces an active catalyst that causes the previously described reactive material to react and/or increase the rate of reaction.

The latent catalyst of the present invention comprises a reaction product formed from components comprising: a ligand; and a metal compound sufficient to catalyze the reactive material. The ligand is derived from a compound comprising a chemical structure represented by any of the previously described Formulas.

As previously described, the latent catalyst of the present invention is also formed from a metal compound sufficient to catalyze the reactive material. As such, the metal compound is selected based on the reactive material such that the metal compound is capable of initiating the reaction of the reactive material or increasing the rate of reaction of the reactive material. It is appreciated that the amount of metal compound sufficient to catalyze a reaction will depend on the reactive materials present (i.e., reaction type) and the specific metal compound.

Non-limiting examples of metal compounds that can be used to form a complex with the ligand include compounds of a transition metal, such as but not limited to a zinc compound, a zirconium compound, a titanium compound, an iron compound, a copper compound, or any combination thereof. Further non-limiting examples of metal compounds suitable to form a complex with the ligand include compounds of Group IIIA metals (such as aluminum compounds), Group IVA metals (such as a tin compound or a lead compound), and Group VA metals (such as a bismuth compound) of the Periodic Table of Chemical Elements.

Specific non-limiting examples of suitable metal compounds sufficient to catalyze the reactive material include metal halides such as metal halide salts, metal carboxylates such as metal carboxylate salts, metal alkoxides, metal triflates, metal sulfonates, metal phosphonates, metal acetylacetonates, metal sulfides, metal oxides, metal mercaptides, metal thioglycolates, metal hydrides, and combinations thereof.

As used herein, a "halide" refers to a compound having one or more halogen atoms bonded to a metal. The term "halide" encompasses ionic compounds (salts) and compounds comprising covalent halogen-metal bonds. Organometallic compounds are also included. Non-limiting examples of suitable halides include: I, Br and Cl compounds of tin(II), tin(IV), (mono, bis, tri) alkyl tin, (mono, bis, tri) aryl tin, zinc, iron, zirconium, and titanium, di-n-butyltindichloride, n-butyltin chloride, tri-n-butyltin chloride, tin (IV) chloride, tin (II) chloride, zinc chloride, zinc bromide, zinc iodide, bismuth chloride, iron chloride, zirconium chloride, titanium tetrachloride, or any combination thereof.

Further, non-limiting examples of metal carboxylate salts include tin, alkyltin, titanium, zinc, zirconium, iron, and bismuth carboxylates. Non-limiting examples of carboxylates include acetate, propionate, butanoate, hexanoate, ethylhexanoate, laurate, and trifluoroacetate.

As used herein, "metal triflate" refers to a metal salt of trifluoromethane sulfonic acid. Non-limiting examples of metal triflates include triflate salts of iron, bismuth, aluminum, zinc, and tin.

A "metal acetylacetonate" refers to a complex between a metal ion and acetylacetonate anion. Non-limiting examples of metal acetylacetonates include tin (II) acetylacetonate, tin (II) hexafluoroacetylacetonate, and manganese acetylacetonate.

Further, non-limiting examples of metal mercaptides include dibutyltin dilaurylmercaptide and dibutyltin bis(2-ethylthioglycolate), and non-limiting examples of metal alkoxides include tin (IV) t-butoxide, titanium (IV) ethoxide, titanium (IV) n-butoxide, titanium (IV) t-butoxide, zirconium (IV) n-butoxide, and zirconium (IV) t-butoxide.

A "metal hydride" refers to a metal compound of a hydride that is formed from the reaction between the metal and a hydride source such as $LiAlH_4$. Non-limiting examples of metal hydrides include tributyl tin hydride and titanium hydride.

The ligand and metal can be combined at a specified molar ratio. For example, the ligand and metal can be combined at a molar ratio of from 0.5:1 to 10:1, or from 0.5:1 to 8:1, or from 0.5:1 to 5:1, or from 1:1 to 2:1.

The latent catalyst can comprise at least 0.001 weight %, at least 0.01 weight %, at least 0.05 weight %, or at least 0.1 weight %, based on the total weight of the composition. Further, the latent catalyst can comprise up to 15 weight %, up to 10 weight %, or up to 5 weight %, based on the total weight of the composition. The latent catalyst can also comprise from 0.001 weight % to 15 weight %, or from 0.01 weight % to 15 weight %, or from 0.05 weight % to 10 weight %, or from 0.1 weight % to 5 weight %, based on the total weight of the composition.

To form the latent catalyst, the previously described ligand and metal compound can be mixed together and reacted to form the final reaction product of the latent catalyst. The ligand and metal compound can be mixed as dry solids or in the absence of free solvent. Alternatively, the ligand and metal compound can be mixed in the presence of free solvent. The free solvent can be a non-aqueous solvent or an aqueous solvent.

As used herein, a "non-aqueous solvent" refers to a liquid medium comprising less than 50 weight % water, based on the total weight of the liquid medium. Such non-aqueous liquid solvents can comprise less than 40 weight % water, or less than 30 weight % water, or less than 20 weight % water, or less than 10 weight % water, or less than 5% water, based on the total weight of the liquid medium. The solvents that make up at least or more than 50 weight % of the liquid medium include organic solvents. Non-limiting examples of suitable organic solvents include polar organic solvents e.g. protic organic solvents such as glycols, glycol ether alcohols, alcohols; and polar aprotic organic solvents such as ketones, glycol diethers, esters, diesters, and combinations thereof. Other non-limiting examples of organic solvents include non-polar organic solvents such as aromatic and aliphatic hydrocarbons.

An "aqueous solvent" refers to a liquid medium comprising 50 weight % or more water, based on the total weight of the liquid medium. Such aqueous liquid solvents can comprise greater than 60 weight % water, or greater than 70 weight % water, or greater than 80 weight % water, or greater than 90 weight % water, or greater than 95% water, based on the total weight of the liquid medium. The solvents that make up less than 50 weight % of the liquid medium include, but are not limited to, any of the previously described organic solvents.

It is appreciated that the ligand binds to the metal compound to form the reaction product of the latent catalyst, which is also referred to herein as a chelate. Without being bound by theory, it is believed that the ligand binds with the metal compound to prevent the metal compound from catalyzing the reactive components. The chelate may form spontaneously upon mixing in solution, or may form upon application of external energy. Upon exposure of actinic radiation, the rate of reaction of the reactive materials increases. Therefore, mixing the latent catalyst in solution or exposing the latent catalyst to actinic radiation causes the ligand to change structure such that the ligand is disassociated from the previously described reaction product to allow the metal product to catalyze the reactive material.

It was also found that a color change can occur during formation and dissociation of at least some of the previously described ligands. Therefore, a color change can indicate the formation of the reaction product or chelate due to the change in structure of the compound that forms the ligand and/or the dissociation of the metal ion from the ligand.

The composition of the present invention can also include other optional materials. For example, the composition can also comprise a colorant. As used herein, "colorant" refers to any substance that imparts color and/or other opacity and/or other visual effect to the composition. The colorant can be added to the coating in any suitable form, such as discrete particles, dispersions, solutions, and/or flakes. A single colorant or a mixture of two or more colorants can be used in the coatings of the present invention.

Example colorants include pigments (organic or inorganic), dyes and tints, such as those used in the paint industry and/or listed in the Dry Color Manufacturers Association (DCMA), as well as special effect compositions. A colorant may include, for example, a finely divided solid powder that is insoluble, but wettable, under the conditions of use. A colorant can be organic or inorganic and can be agglomerated or non-agglomerated. Colorants can be incorporated into the coatings by use of a grind vehicle, such as an acrylic grind vehicle, the use of which will be familiar to one skilled in the art.

Examples of suitable pigments and/or pigment compositions include carbazole dioxazine crude pigment, azo, monoazo, disazo, naphthol AS, salt type (lakes), benzimidazolone, condensation, isoindolinone, isoindoline and polycyclic phthalocyanine, quinacridone, perylene, perinone, diketopyrrolo pyrrole, thioindigo, anthraquinone, indanthrone, anthrapyrimidine, flavanthrone, pyranthrone, anthanthrone, dioxazine, triarylcarbonium, quinophthalone pigments, diketo pyrrolo pyrrole red ("DPPBO red"), carbon black, and mixtures thereof. The terms "pigment" and "colored filler" can be used interchangeably.

Example dyes include those that are solvent and/or aqueous based such as acid dyes, azoic dyes, basic dyes, direct dyes, disperse dyes, reactive dyes, solvent dyes, sulfur dyes, mordant dyes, for example, bismuth vanadate, anthraquinone, perylene, aluminum, quinacridone, thiazole, thiazine, azo, indigoid, nitro, nitroso, oxazine, phthalocyanine, quinoline, stilbene, and triphenyl methane.

Example tints include, but are not limited to, pigments dispersed in water-based or water miscible carriers such as AQUA-CHEM 896 commercially available from Degussa, Inc., CHARISMA COLORANTS and MAXITONER INDUSTRIAL COLORANTS commercially available from Accurate Dispersions Division of Eastman Chemical, Inc.

Other non-limiting examples of materials that can be used with the compositions of the present invention include plasticizers, abrasion resistant particles, fillers including, but not limited to, micas, talc, clays, and inorganic minerals, anti-oxidants, hindered amine light stabilizers, UV light absorbers and stabilizers, surfactants, flow and surface control agents, thixotropic agents, organic cosolvents, corrosion-inhibitors, reactive diluents, catalysts, reaction inhibitors, and other customary auxiliaries.

The compositions of the present application can be used in a variety of applications. For example, the compositions can be used to form a coating over at least a portion of a substrate. The compositions can be applied to a wide range of substrates known in the coatings industry and cured to form a coating. As used herein, the terms "curable", "cure", and the like mean that at least a portion of the materials of the reactive material in a composition is crosslinked or crosslinkable. The compositions are at least partially cured with the use of actinic radiation as previously described. However, additional processes can be used to help cure the coating including, but not limited to, heat.

The compositions of the present invention can be applied and cured to form a coating, for example, over automotive substrates (e.g. automotive vehicles including but not limited to cars, buses, trucks, trailers, etc.), industrial substrates, aerocraft and aerocraft components, marine substrates and components such as ships, vessels, and on-shore and off-shore installations, storage tanks, windmills, nuclear plants, packaging substrates, wood flooring and furniture, apparel, electronics, including housings and circuit boards, glass and transparencies, sports equipment, including golf balls, stadiums, buildings, bridges, and the like. These substrates can be, for example, metallic or non-metallic. Metallic substrates include, but are not limited to, tin, steel (including electrogalvanized steel, cold rolled steel, hot-dipped galvanized steel, steel alloys, or blasted/profiled steel, among others), aluminum, aluminum alloys, zinc-aluminum alloys, steel coated with a zinc-aluminum alloy, and aluminum plated steel. As used herein, blasted or profiled steel refers to steel that has been subjected to abrasive blasting and which involves mechanical cleaning by continuously impacting the steel substrate with abrasive particles at high velocities using compressed air or by centrifugal impellers. The abrasives are typically recycled/reused materials and the process can efficiently removal mill scale and rust. The standard grades of cleanliness for abrasive blast cleaning is conducted in accordance with BS EN ISO 8501-1.

Further, non-metallic substrates include polymeric, plastic, polyester, polyolefin, polyamide, cellulosic, polystyrene, polyurethane polyacrylic, poly(ethylene naphthalate), polypropylene, polyethylene, nylon, EVOH, polylactic acid, other "green" polymeric substrates, poly(ethylene terephthalate) (PET), polycarbonate, composite polymeric substrates comprising glass and/or carbon fiber, polycarbonate acrylobutadiene styrene (PC/ABS), polyamide, wood, veneer, wood composite, particle board, medium density fiberboard, cement, stone, glass, paper, cardboard, textiles, leather both synthetic and natural, and the like.

When glass is used as the substrate, the glass can include any type of glass such as soda-lime-silicate glass, borosilicate glass, or leaded glass. The glass can be clear glass such as non-tinted or non-colored glass. Alternatively, the glass can be tinted or otherwise colored glass. The glass can be annealed or heat-treated glass. As used herein, the term "heat treated" means tempered or at least partially tempered. The glass can be of any type, such as conventional float glass, and can be of any composition having any optical properties, e.g., any value of visible transmission, ultraviolet transmission, infrared transmission, and/or total solar energy transmission. Further, as used herein, the term "float glass" refers to glass formed by a conventional float process in which molten glass is deposited onto a molten metal bath and controllably cooled to form a float glass ribbon.

The coatings formed from the compositions of the present invention can be applied to a substrate as a monocoat. As used herein, a "monocoat" refers to a single layer coating system that is free of additional coating layers. Thus, the composition of the present invention can be applied directly to a substrate and cured to form a single layer coating, i.e. a monocoat.

Alternatively, the coating formed from the compositions of the present invention can be applied to a substrate along with additional coating layers, such as a second coating layer, to form a multi-layer coating system. It is appreciated that the multi-layer coating can comprise multiple coating layers such as three or more, or four or more, or five or more, coating layers. Further, each coating composition can be applied as a dry-on-dry process where each coating composition is dried or cured to form a coating layer prior to application of another composition coating. Alternatively, all or certain combinations of each coating composition described herein can be applied as a wet-on-wet process and dried or cured together.

The coatings formed from the compositions can also be applied as a direct gloss coating. As used herein, a "direct gloss coating" is a topcoat in which additional coatings can be applied to the substrate prior to application of the direct gloss coating, such as a primer for example. Further, the direct gloss coating is typically a pigmented coating of a desired gloss, which may be in the range of low to high.

The compositions of the present invention can be applied by any means standard in the art, such as electrocoating, spraying, electrostatic spraying, dipping, rolling, brushing, and the like. It is appreciated that the coatings can also be applied in dry forms such as powder or films.

The compositions of the present invention can be 3-D printed, or applied to the interior of a mold, to achieve a dimensional article such as an optical article or molded part. Non-limiting examples of optical articles include ophthalmic articles such as plano (without optical power) and vision correcting (prescription) lenses (finished and semi-finished) including multifocal lenses (bifocal, trifocal, and progressive lenses); and ocular devices such as contact lenses and intraocular lenses, sun lenses, fashion lenses, sport masks, shields, and goggles. The optical article also may be chosen from glazings such as architectural windows and vehicular transparencies such as automobile or aircraft windshields and side windows.

Optionally, the compositions can be placed into a mold to form an article. In such processes, a mold release agent can also be added to the composition. As used herein, a "mold release agent" refers to a component that aids in removing a cured composition from a mold. Non-limiting examples of suitable mold release agent include dibutyl phosphate, dioctyl phosphate, bis-(2-ethylhexyl)phosphate, dimethylphosphate, diethylphosphate, diisopropylphosphate, dibutylphosphate, dioctylphosphate, bis(2-ethylhexyl)phosphate, diisodecylphosphate, methoxyethylethoxy ethy lphosphate, methoxy ethyl-propoxyethylphosphate, ethoxyethylpropoxyethyl phosphate, ethoxy ethy 1-butoxy ethyl phosphate, di(methoxyethyl) phosphate, di(ethoxyethyl)phosphate, di(propoxyethyl) phosphate, di(butoxyethyl) phosphate, di(hexyloxyethyl) phosphate, di(decyloxyethyl) phosphate, di(methoxypropyl) phosphate, di(ethoxypropyl) phosphate, di(propoxypropyl)phosphate, and/or mixtures of the same.

As indicated, the compositions can also be used to form a polymeric sheet. As used herein, a "polymeric sheet" refers to a pre-formed film having a generally uniform thickness and capable of self-support. The film could be laminated onto or into other multi-layer articles.

The present invention is also directed to a method of irradiating a composition comprising the reactive material and latent catalyst previously described. As indicated, the method includes irradiating the composition with actinic radiation such that the ligand is disassociated from the reaction product. Further, the composition can be applied to at least a portion of a surface of a substrate or to an interior portion of a mold prior to irradiating the composition. The composition can then be irradiated to help form the final coating or article. Alternatively, the composition can be applied to at least a portion of a surface of a substrate or to an interior portion of a mold after irradiating the composition. The irradiated composition can then be subjected to further processing such as by exposing the irradiated composition to further irradiation and/or heat, for example.

It is appreciated that for any of the application options the composition can be irradiated prior to, during, or after application. Also, for all options, additional thermal, infrared or microwave energy may be employed to increase the rate of reaction or initiate the catalysis. Further, the composition is irradiated at a wavelength, intensity and duration sufficient to effect ejection of the complexed metal ion. The irradiation source may be a broadband source such as fluorescent or incandescent lamps, or sunlight, or a narrow wavelength source such as a light emitting diode (LED) or a laser.

As previously noted, the irradiation source may comprise visible light. The wavelength(s) of this irradiation source may overlap at least partially with the absorption spectrum of the latent catalyst (e.g., if the complex has a high degree of absorption in the blue portion of the spectrum, the use of a blue irradiation source could be used).

It was found that the compositions of the present invention exhibit an increased reaction rate between one or more reactive materials that form at least a portion of the composition, while also exhibiting an extended pot life. By providing both rapid cure rates and an extended pot life, the compositions of the present invention remain stable for longer periods of time but can be cured on demand.

The following examples are presented to demonstrate the general principles of the invention. The invention should not be considered as limited to the specific examples presented. All parts and percentages in the examples are by weight unless otherwise indicated.

Examples 1-8

Preparation of a Latent Catalyst

Part A: A first ligand was first prepared by mixing 5-Chloro-8-hydroxyquinoline (9 g), hexamethylenetetramine (14 g), and trifluoroacetic acid (150 mL). The mixture was sparged with nitrogen for 15 minutes, heated at reflux for eight hours, then cooled to room temperature. Concentrated HCl (60 mL) and water (200 mL) were added, and the mixture was stirred for 16 hours, followed by neutralization with a sodium hydroxide solution to a pH of 5. The solution was extracted twice with 200 mL chloroform, dried over sodium sulfate, then purified by column chromatography with silica gel, eluting with a 3:2 (v:v) mixture of ethyl acetate and chloroform, then recrystallized from a mixture of chloroform and ethyl acetate to yield 3.3 g solid product. Mass spectroscopy indicated a product consistent with 5-chloro-8-hydroxyquinoline-7-carboxaldehyde.

The resulting product (1.0 g), 1,3,3-trimethyl-2-methyleneindoline (0.83 g), and 2-butanone (20 mL) were mixed, heated at reflux for eight hours, then cooled to room temperature. Filtration yielded a colorless solid. Mass spectroscopy and nuclear magnetic resonance spectroscopy indicated a product consistent with the following structure.

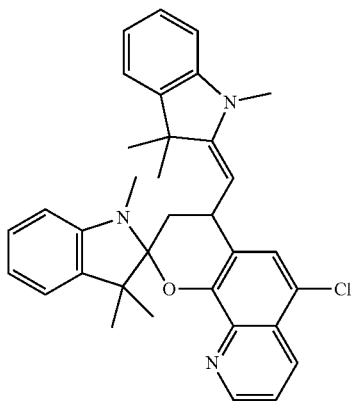

A second ligand was further prepared by mixing Ligand 1 (1.0 g), pyridine (25 mL), and 1,3,3-trimethyl-2-methyleneindoline (0.83 g) and heated at reflux for eight hours. The mixture was cooled to room temperature and concentrated under vacuum. Ethanol was added, and a white precipitate was filtered from the mixture. The filtrate was concentrated under vacuum, and a blue solid was recrystallized from a mixture of hexanes and ethyl acetate. Nuclear magnetic resonance spectroscopy indicated a product consistent with 6'-chloro-1,3,3-trimethylspiro[indoline-2,2'-[3,2-h]pyrido[2H-1]benzopyran].

Part B: The first ligand of Part A and different metal compounds were next mixed with sufficient acetone to suspend and disperse the materials. The formation of a chelate was indicated by a color change as noted in Table 1.

TABLE 1

| Example | Metal Compound | Parts by weight (pbw) of metal compound | Pbw first ligand of Part A | Pbw of Acetone | Solution color |
|---|---|---|---|---|---|
| Example 1 | Dibutyltin dichloride | 0.409 | 1.0 | 54.7 | Purple |
| Example 2 | K-KAT ® 348[1] | 1.15 | 1.0 | 84.0 | Red-purple |
| Example 3 | 8% Zinc HEX-CEM ®[2] | 1.09 | 1.0 | 7.45 | Blue-purple |
| Example 4 | Iron(III) chloride hexahydrate | 0.36 | 1.0 | 54.5 | Pink-purple |
| Example 5 | Dibutyltin diacetate | 0.57 | 1.0 | 60.0 | Purple |
| Example 6 | Zinc chloride | 0.18 | 1.0 | 46.2 | Purple |
| Example 7 | Zirconium tetrachloride | 0.32 | 1.0 | 51.4 | Purple |

[1]Bismuth carboxylate catalyst, reported to contain 25% metal, available from King Industries.
[2]Zinc 2-ethylhexanoate diluted in mineral spirits to contain 8% zinc, available from OMG Borchers GmbH.

The second ligand of Part A was also mixed with dibutyltin dichloride and sufficient acetone to suspend and disperse the materials. The formation of a chelate was indicated by a color change as noted in Table 2.

TABLE 2

| Example | Metal Compound | Parts by weight (pbw) of metal compound | Pbw second ligand of Part A | Pbw of Acetone | Solution color |
|---|---|---|---|---|---|
| Example 8 | Dibutyltin dichloride | 0.444 | 1.0 | 55.7 | Purple |

Example 9

Preparation of Compositions Containing Reactive Materials

Part A: Several compositions containing reactive materials were prepared from the components listed in Table 3.

TABLE 3

| | Component | Composition (Parts by Weight of Components) | | |
|---|---|---|---|---|
| | | Sample A | Sample B | Sample C |
| Charge 1 | SETALUX ® 1909 BA-75[3] | 41.3 | | |
| | Acrylic Polyol A[4] | | 35.1 | 34.4 |
| | Acrylic Polyol B[5] | | 16.1 | 15.7 |
| | BYK ®-300[6] | 0.2 | 0.2 | 0.2 |
| | ADDITOL ® VXL 4930[7] | | 0.1 | 0.2 |
| | TINUVIN ® 123[8] | | | 1.0 |
| | EVERSORB ® 74[9] | | | 0.7 |
| | Acetone | 5.9 | 3.5 | 3.4 |
| | Methyl amyl ketone | 5.0 | 3.2 | 3.1 |
| | Methyl isobutyl ketone | | 6.4 | 6.3 |
| | Propylene glycol monomethyl ether acetate | 8.4 | 5.8 | 5.7 |
| | Xylene | 19.4 | 13.7 | 13.4 |
| Charge 2 | DESMODUR ® N 3300A[10] | 19.9 | 15.9 | 16.0 |

[3]An acrylic polyol in butyl acetate, available from Nuplex.
[4]A copolymer of isostearic acid, hydroxypropyl acrylate, methyl methacrylate, styrene, and glycidyl methacrylate (22.4%/23.3%/10.7%/32.4%/11.2% by weight) at 58.8% solids in xylene.
[5]An acrylic polyol prepared in accordance with Example 1 in U.S. Pat. No. 6,458,885, which is incorporated herein by reference.
[6]A polyether modified polydimethylsiloxane available from BYK USA, Inc.
[7]A polyether modified silicone defoamer available from Allnex.
[8]A hindered amine light stabilizer available from BASF SE.
[9]A UV absorber available from Everlight Chemical Industrial Corp.
[10]Aliphatic polyisocyanate based on hexamethylene diisocyanate trimer, available from Covestro AG.

For each of Samples A-C, the components of Charge 1 were added to a suitable flask, and mixed under agitation. Charge 2 was then added, and the compositions were mixed to homogeneity.

Part B: A pigmented composition containing reactive materials was also prepared from the components listed in Table 4. The composition was prepared in a similar manner as the compositions of Part A.

TABLE 4

| | Component | Sample D Parts by weight |
|---|---|---|
| Charge 1 | Acrylic Polyol B[5] | 19.2 |
| | Barium Sulfate | 9.6 |
| | ASP ® 200[11] | 5.5 |
| | ACEMATT ® OK 412[12] | 0.3 |
| | NICRON ® 665[13] | 9.1 |
| | RAVEN ® 410[14] | 0.1 |
| | TIONA ® 595[15] | 9.1 |
| | NUOSPERSE ® 657 NA[16] | 0.1 |
| | N-Butyl acetate | 18.3 |
| | Methyl amyl ketone | 0.8 |
| | Propylene glycol monomethyl ether acetate | 2.8 |
| | Xylene | 19.2 |
| Charge 2 | DESMODUR N 3300A[10] | 5.9 |

[11]Kaolin available from BASF SE.
[12]A matting agent available from Evonik Resource Efficiency GmbH.
[13]A platy, high purity talc available from Imerys.
[14]Carbon Black pigment available from Columbian Chemicals.
[15]Titanium dioxide available from Nexeo Solutions.
[16]Dispersing agent from Elementis Specialties.

Examples 10-21

Preparation of Compositions Containing Reactive Materials and Latent Catalysts Compositions containing reactive materials and latent catalysts were prepared from the components listed in Table 5.

TABLE 5

| | Components (Parts by Weight) | | | | | |
|---|---|---|---|---|---|---|
| | Composition with reactive material | | Catalyst | | | |
| Example | (100 Parts by Weight) | Dibutyltin dichloride | Ex. 1 | K-KAT 348 ®[1] | Ex. 2 | Ex. 8 |
| Comparative Example 10 | Sample A | 0 | 0 | 0 | 0 | 0 |
| Comparative Example 11 | Sample B | 0 | 0 | 0 | 0 | 0 |
| Comparative Example 12 | Sample A | 0.06 | 0 | 0 | 0 | 0 |
| Comparative Example 13 | Sample B | 0.05 | 0 | 0 | 0 | 0 |
| Comparative Example 14 | Sample B | 0 | 0 | 0.13 | 0 | 0 |
| Comparative Example 15 | Sample D | 0.01 | 0 | 0 | 0 | 0 |
| Example 16 | Sample A | 0 | 7.3 | 0 | 0 | 0 |
| Example 17 | Sample B | 0 | 5.8 | 0 | 0 | 0 |
| Example 18 | Sample C | 0 | 5.8 | 0 | 0 | 0 |
| Example 19 | Sample B | 0 | 0 | 0 | 12.9 | 0 |
| Example 20 | Sample D | 0 | 1.6 | 0 | 0 | 0 |
| Example 21 | Sample A | 0 | 0 | 0 | 0 | 7.1 |

Immediately after preparing Samples A-D, the catalyst, if any, was added to each mixture.

Example 22

Evaluation of Gel Time

Once the compositions of Examples 10-21 are mixed, they begin to react causing the bulk solution viscosity to increase. The period of time, beginning at mixing and ending when the composition gels, is referred to as a gel time. Compositions that have longer gel times are advantageous because they provide greater application flexibility.

Gel time was measured by monitoring the viscosity of each composition after mixing, using a Brookfield CAP 2000 viscometer with a #1 spindle at 900 RPM and 25° C.

When viscosities increased above 200 cP, the viscosity was monitored visually until no flow was observed for at least five seconds. The results are reported in Table 6.

TABLE 6

| Composition | Time to Gelation (hours) |
|---|---|
| Comparative Example 10 | >24 |
| Comparative Example 11 | >24 |
| Comparative Example 12 | 1 |
| Comparative Example 13 | 2 |
| Comparative Example 15 | 1.5 |
| Example 16 | 24 |
| Example 17 | >24 |
| Example 17A [17] | 21 |
| Example 18 | >5 |
| Example 20 | >3 |
| Example 21 | >20 |

[17] The composition of Example 17 was also exposed to 530 nm irradiation for 10 minutes prior to testing as Example 17A.

As shown in Table 6, the compositions of the present invention have gel times similar to the uncatalyzed comparative examples, even though the inventive compositions contain the same molar amount of tin as the catalyzed comparative examples. Additionally, gel times for the compositions of present invention are much longer than comparative examples with dibutyl tin dichloride. Long gel times with cure initiated after irradiation define a further advantage.

Example 23

Evaluation of Composition Catalysis

Coatings were formed from each of the compositions of Examples 10-21 by first applying each composition to a 4 by 6 inch (10.16 cm by 15.24 cm) ED6060 cold rolled steel panels, available from ACT Test Panel Technologies. A draw down bar with a 5 mil gap was used to provide 0.5 to 1 mil dry film thickness. The coated panels were subjected to thermal and light conditions. "Dark" indicates the panel was placed in an unlit chamber at 25° C. for the duration of the testing. "Ambient" conditions indicates the panel was placed in an open laboratory with fluorescent lighting at approximately 25° C. for the duration of the testing. "Dark heated" indicates the panel was placed in a 50° C. oven for the designated amount of time, followed by the "dark" conditions above for the remainder of the time. "Irradiated" indicates the panel was placed under a 530 nm LED light source situated 8 cm above the panel surface, at 50° C. for the time indicated, followed by the "ambient" conditions described above for the remainder of the time.

Further, the "Dust-free Time" for each coating was determined as the time at which no cotton fibers adhered to the coating surface after placing a cotton ball on the surface by dropping the cotton ball from a height of approximately 5 cm, leaving the cotton ball in place for 5 seconds, and inverting the panel to remove the cotton ball. Under all conditions, Comparative Examples 10 and 11, which had no metal catalyst present, exceeded 240 minutes for dust free time at which time the testing was discontinued.

Table 7 demonstrates the dust free time of tin containing formulations, and Table 8 demonstrates the dust free time of bismuth containing formulations. Dust free time is used to gauge completeness of surface cure.

TABLE 7

| | Dust Free Time (min) | | | |
|---|---|---|---|---|
| Composition | Dark | Ambient | Dark heated, 5 minutes | Irradiated 5 minutes |
| Comparative Example 12 | 30 | 28 | 17 | 15 |
| Comparative Example 13 | 30 | 30 | 18 | 18 |
| Example 16 | 108 | 48 | 108 | 18 |
| Example 17 | 120 | 47 | 120 | 19 |
| Example 17A[17] | 89 | 56 | | |
| Example 18 | 121 | | | 14 |
| Example 21 | | >300 | | 34.5 |

TABLE 8

| | Dust Free Time (min) | | | |
|---|---|---|---|---|
| Composition | Dark | Ambient | Dark heated, 15 minutes | Irradiated 15 minutes |
| Comparative Example 14 | 170 | 170 | 22-23 | 20 |
| Example 19 | 231 | 168 | 69 | 22-23 |

As shown in Tables 7 and 8, the compositions of the present invention comprising a ligand and a tin metal compound or a ligand and a bismuth metal compound exhibited significantly increased cure rates, similar to tin or bismuth catalyzed comparative examples when irradiated for 5 or 15 minutes. Additionally, Tables 7 and 8 show that these increased cure rates are not due to thermal energy.

Example 24

Evaluation of Cured Coatings

Polyurethane (hydroxyl-isocyanate reacted material) pigmented compositions of Comparative Example 15 and Example 20 were subjected to cure conditions as follows to form a cured coating: "dark" was treated by heating at 50° C. for 10 minutes followed by ambient temperatures, all in a dark environment; and "irradiated" was placed under a 530 nm LED light source situated 8 cm above the panel surface, at 50° C. for 10 minutes, followed by the "ambient" conditions as previously described for the remainder of the time. The degree of cure (crosslinking) was reported as "MEK Double Rubs," determined by rubbing the surface of the film with a cotton swab soaked with methyl ethyl ketone (MEK) until breakthrough of the film to the panel surface is observed. The test was discontinued after 100 double rubs were performed without penetration. The higher double rubs indicate a greater degree of cure.

As shown in FIG. 1, the coating formed from the composition of Example 20 of the present invention exhibited a degree of cure similar to Comparative Example 15 only when irradiated. The long gel time with accelerated cure only after irradiation illustrates advantages of the present invention.

MEK Double Rubs were also used to test the solvent resistance of the compositions of Comparative Examples 10 and 12 and Example 21. Each of the compositions were evaluated after 5.5 hours after the samples were subjected to the cure conditions indicated in Table 9.

TABLE 9

| Example | MEK Double Rubs after 5.5 h | |
|---|---|---|
| | Dark Heated 5 minutes | Irradiated 5 minutes |
| Comparative Example 10 | 10 | 10 |
| Comparative Example 12 | 100 | 100 |
| Example 21 | 10 | 80 |

As shown in Table 9, the coating formed from the composition of Example 21 of the present invention exhibited a degree of cure similar to the tin catalyzed composition of Comparative Example 12 only when irradiated. The ability to provide long gel times with accelerated cure only after irradiation in pigmented compositions illustrates advantages of the present invention.

Examples 25-27

Evaluation of Cured Coatings

Curable compositions formed from an acid functional component and an epoxy functional component were first prepared according to Table 10.

TABLE 10

| | | Parts By Weight | | |
|---|---|---|---|---|
| | Component | Comparative Example 25 | Comparative Example 26 | Example 27 |
| Charge 1 | Acetone | 2.28 | 2.28 | 2.28 |
| | JONCRYL ® 819[18] | 1.12 | 1.12 | 1.12 |
| Charge 2 | EPON ® 1001-X-75[19] | 1.00 | 1.00 | 1.00 |
| Charge 3 | 8% Zinc HEX-CEM ® | 0 | 0.06 | 0 |
| | Catalyst of Example 3 | 0 | 0 | 0.53 |

[18]A carboxylic acid functional acrylate resin available from BASF SE.
[19]An epoxy functional resin supplied at 75% solids in xylene available from Momentive Specialty Chemicals, Inc.

The curable compositions of Examples 25-27 were prepared by adding charge 2 to the combined ingredients in charge 1. Where applicable, charge 3 was added to the homogeneous solution and mixed immediately prior to applying to a panel as described in Example 23.

The coated panels were subjected to the "dark" and "irradiated" conditions as described previously for 10 minutes prior to evaluation by MEK double rubs as also described above. The same panels were then placed into an oven at 140° C. for 15 minutes. MEK double rubs were then performed.

Following the MEK double rubs, the two sets were then placed in a 140° C. oven for 15 minutes and cooled to room temperature for five minutes ("+Thermal"). The coatings were again tested with MEK double rubs. The results are reported in Table 11.

TABLE 11

| | Dark | | Irradiated | |
|---|---|---|---|---|
| | Dark only | + Thermal | Irradiated only | + Thermal |
| Comparative Example 25 | 0 | 10 | 0 | 10 |
| Comparative Example 26 | 0 | 25 | 0 | 20 |
| Example 27 | 0 | 10 | 0 | 26 |

As shown in Table 11, the composition of Example 27 exhibits similar cure to the catalyzed composition of Comparative Example 26, only after irradiation. The light initiated cure of different active hydrogen components and components reactive with active hydrogen components, including the carboxylic acid and epoxy components of the compositions in Table 10 illustrates advantages of the present invention.

Examples 28-30

Evaluation of Cured Coatings

Curable compositions formed from a thiol functional component and a vinyl ether functional component were first prepared according to Table 12.

TABLE 12

| | | Parts By Weight | | |
|---|---|---|---|---|
| | Component | Comparative Example 28 | Comparative Example 29 | Example 30 |
| Charge 1 | Butyl acetate | 1.89 | 1.7 | 1.61 |
| | 1,4-Cyclohexane dimethanol divinyl ether | 2.49 | 2.49 | 2.49 |
| | BYK ®-300[20] | 0.05 | 0.05 | 0.05 |
| Charge 2 | Pentaerythritol Tetra (3-mercaptopropionate) | 3.1 | 3.1 | 3.1 |
| Charge 3 | Iron trichloride hexahydrate | 0 | 0.002 | 0 |
| | Catalyst of Example 4 | 0 | 0 | 0.28 |

[20]Silicone surface additive from BYK USA, Inc.

The curable compositions of Examples 28-30 were prepared by adding charge 2 to the combined ingredients in charge 1 according to the amounts indicated in Table 12. Where applicable, charge 3 was added to the homogeneous solution and mixed thoroughly. The composition of Comparative Example 29 gelled immediately upon adding the iron catalyst.

After the compositions were thoroughly mixed, each composition was divided into two vials. One vial of each composition was placed in the dark for 30 minutes and listed in Table 13 as "Dark." The second vial of each composition was exposed to 530 nm LED light source at 50° C. for 30 minutes, listed in Table 13 as "Irradiated." After exposure to the dark or irradiated condition, the compositions were applied to panels as described in Example 23 and evaluated for Dust Free Time under ambient lighting conditions as previously described. The dust free times for the coatings are reported in Table 13.

TABLE 13

| | Dust Free Time (min) | |
|---|---|---|
| Composition | Dark | Irradiated |
| Comparative Example 28 | >240 | >240 |
| Example 30 | >150 | 45 |

As shown in Table 13, the composition of Example 30 exhibited significantly increased cure rates when irradiated for five minutes. Additionally, the composition of Example 30 did not immediately gel as with Comparative Example 29, despite comprising an equal molar amount of iron. The light initiated cure of different types of reactive components, including the cationic polymerizable components of the compositions in Table 12, is yet a further advantage of the present invention.

Example 31

Preparation of a Ligand

Part A: A solution of 3-methylbutan-2-one (4.93 g) and 2-(4-methoxyphenyl)hydrazin-1-ium chloride (10.0 g) in ethanol (100 mL) was heated under reflux for 5 hours. Then the solvent was distilled off under reduced pressure. The residue was dissolved in dichloromethane and washed with water. The organic phase was dried over magnesium sulfate, and the solvent was distilled off under reduced pressure.

Part B: The product of Part A (10.79 g) and methyl iodide (4.1 mL) were taken into acetonitrile (100 mL). The reaction mixture was heated under reflux and nitrogen atmosphere for 24 hours. After cooling the mixture down to ambient temperature, the solvent was distilled off under reduced pressure.

Part C: A solution of the product of Part B (10.0 g) in acetonitrile (50 mL), water (50 mL) and aqueous potassium hydroxide (2.0 g in 20 mL water) was stirred at ambient temperature for 1 hour. Then the mixture was washed with methylene chloride (100 mL) and the organic layer was dried over MgSO4. The solvent was distilled off under reduced pressure.

Part D: The product of Part C (0.5 g) was dissolved in 20 ml of anhydrous pyridine and stirred for 5 minutes at room temperature. Then 5-methoxy-1,3,3-trimethyl-2-methyleneindoline (0.4 g) was added into the mixture and heated to reflux under nitrogen. The mixture was refluxed for additional 8 hours under nitrogen. After that HPLC of the reaction mixture was checked and found no starting material was left. The reaction mixture was cooled to room temperature and the solvent was evaporated out under reduced pressure. Residue was taken into acetonitrile and passed through a short silica plug using acetonitrile as an eluting solvent. Desired fractions were collected and solvent was evaporated under reduced pressure. The dark colored solid was filtered and washed with hexanes. After drying in vacuum oven ~0.65 g (yield—69%) of solid was isolated that is 6'-chloro-5-methoxy-1,3,3-trimethylspiro[indoline-2, 2'-pyrano[3,2-h]quinoline], as confirmed by 1H NMR.

Example 32

Preparation of a Ligand

The product 5-chloro-8-hydroxyquinoline-7-carbaldehyde (0.5 g) prepared in Part A of Example 1 was dissolved in 20 ml of anhydrous pyridine and stirred for 5 minutes at room temperature. Then 5-chloro-1,3,3-trimethyl-2-methyleneindoline (0.4 g) was added into the mixture and the solution heated to reflux under nitrogen. The mixture was refluxed for additional 8 hours under nitrogen. The reaction mixture was cooled to room temperature and the solvent was evaporated out under reduced pressure. Residue was dissolved in acetonitrile and passed through a short silica plug using acetonitrile as the eluting solvent. The desired fractions were collected and solvent was evaporated out under reduced pressure. The Dark colored solid was filtered and washed with hexanes and after drying in vacuum oven ~0.5 g (yield—54%) of solid was isolated that is 5,6'-dichloro-1,3,3-trimethylspiro[indoline-2,2'-pyrano[3,2-h]quinoline], as confirmed by 1H NMR.

Example 33

Preparation of a Ligand

The product 5-bromo-8-hydroxyquinoline-7-carbaldehyde was first made by following the same procedure described in Part A of Examples 1-8 to make 5-chloro-8-hydroxyquinoline-7-carboxaldehyde, except 5-bromoquinolin-8-ol was used instead of 5-chloroquinolin-8-ol. The 5-bromo-8-hydroxyquinoline-7-carbaldehyde (0.5 g) was then taken into 20 ml of anhydrous pyridine and stirred for 5 minutes at room temperature. Solid material went into the solution on stirring. Then 1,3,3-trimethyl-2-methyleneindoline (1.03 g) was added and the mixture was heated to reflux under nitrogen. The reaction mixture was refluxed for additional 8 hours under nitrogen. The reaction mixture was cooled to room temperature and off-white solid was precipitated out from pyridine solution overnight. The solid was filtered and washed with ethanol and after drying in vacuum oven 0.4 g (yield—35%) of solid was isolated that was (Z)-6'-bromo-1,3,3-trimethyl-4'-(1,3,3-trimethylindolin-2-ylidene)methyl)-3',4'-dihydrospiro[indoline-2,2'-pyrano[3, 2-h]quinoline], as confirmed by 1H NMR.

Example 34

Preparation of Latent Catalysts

The ligands made in the Examples 31-32 and dibutyltin dichloride (DBTDC) were mixed with acetone. Then diethylene glycol and DESMODUR® N 3200A were added into the mixture. The solution was then stirred using a vortex mixer. The amounts of the materials in the composition are listed in Table 14.

TABLE 14

| Examples | Component | Amount (grams) |
| --- | --- | --- |
| Comparative Sample 1 | Diethylene Glycol | 1.02 |
| | DESMODUR ® N 3200A [10] | 3.71 |
| | Acetone | 1.18 |
| | DBTDC | 0.0047 |
| Sample 2 | Diethylene Glycol | 1.0286 |
| | DESMODUR ® N 3200A [10] | 3.7310 |
| | Acetone | 1.1889 |
| | DBTDC | 0.0055 |
| | Example 31 | 0.0138 |
| Sample 3 | Diethylene Glycol | 1.0060 |
| | DESMODUR ® N 3200A [10] | 3.7438 |
| | Acetone | 1.1840 |
| | DBTDC | 0.0055 |
| | Example 31 | 0.0137 |
| Sample 4 | Diethylene Glycol | 1.0056 |
| | DESMODUR ® N 3200A [10] | 3.7238 |
| | Acetone | 1.1817 |
| | DBTDC | 0.0053 |
| | Example 32 | 0.0132 |
| Sample 5 | Diethylene Glycol | 1.0290 |
| | DESMODUR ® N 3200A [10] | 3.7420 |
| | Acetone | 1.1838 |
| | DBTDC | 0.0056 |
| | Example 32 | 0.0139 |

Example 35

Evaluation of Latent Catalysts

ATR-FTIR spectra of Samples 1-5 in Example 34 were collected with a Pike MIRacle diamond ATR™ from Pike Technologies on a BRUKER Vertex 70 FTIR. A drop of the formulations were placed in the liquid cup on the ATR crystal, and spectra were collected at 5 minute intervals for 1 hour at ambient temperature. To prevent solvent evaporation, the sample was covered with either a metal lid (Dark condition) or a glass slide (Light condition) A fiber optic illuminator with 150W quartz halogen bulb was utilized to continuously illuminate samples for the "Light" condition. Background and sample scans (128) were collected at 4 cm-1 resolution with a DLaTGS detector. The reaction of the isocyanate group was monitored by monitoring its absorption at 2270 cm-1. The percentage conversion of the isocyanate group was calculated by the ratio of the absorption at 2270 cm-1 after 60 minutes and the initial absorption at 2270 cm-1. The results are illustrated in Table 15.

TABLE 15

| Sample | Ligand:Tin Ratio | Conditions | % NCO Conversion at 60 min |
|---|---|---|---|
| Comparative 1 | — | Dark | 75.9 |
| 2 | 2:1 | Dark | 8.5 |
| 3 | 2:1 | Light | 54.0 |
| 4 | 2:1 | Dark | 27.6 |
| 5 | 2:1 | Light | 58.1 |

The IR cure study described above shows that under dark conditions the experimental samples with the ligand decrease the reaction rate as compared to Comparative Sample 1 with no ligand. Upon exposure the visible light source, the reaction rate was increased. This highlights the ability of present invention to increase reaction when exposed to light while maintaining good pot life in the dark.

The present invention is also directed to the following clauses.

Clause 1: A compound capable of coordinating with a metal comprising a chemical structure represented by Formula (II)-B,

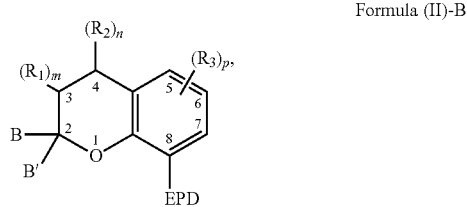

Formula (II)-B wherein, EPD represents a group comprising an electron pair donor atom;
B and B' are each independently an aryl group, a heteroaryl group, an alkenyl group, or alkynyl group, or B and B' taken together form a spirocyclic group;
$R_1$ and $R_2$ each independently comprise a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, a spirocyclic group, or any combination thereof, or $R_1$ and $R_2$ together form a cycloalkyl group or a heterocyclic group;
each $R_3$ independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof;
m and n are each independently a number selected from 0 to 2; and
p is a number selected from 0 to 3.

Clause 2: The compound of clause 1, wherein the electron pair donor atom comprises a nitrogen atom, an oxygen atom, a phosphorus atom, or a carbene, preferably a nitrogen atom.

Clause 3: The compound of clauses 1 or 2, wherein the EPD of Formula (II)-B comprises a cyclic ring comprising at least one of a nitrogen atom, an oxygen atom, and/or a phosphorus atom, preferably a nitrogen atom.

Clause 4: The compound of any of clauses 1-3, wherein $R_1$ and $R_2$ each independently comprise an alkyl group, an aryl group, a halo group, an alkenyl group, or an alkynyl group.

Clause 5: The compound of any of clauses 1-4, wherein B and B' taken together form a spirocyclic group comprising a nitrogen, an oxygen, or a sulfur atom, preferably a nitrogen atom.

Clause 6: The compound of any of clauses 1-5, wherein a substituent of each carbon atom located at positions 5-7 independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof.

Clause 7: The compound of any of clauses 1-5, wherein a substituent of a carbon atom at one of positions 5-7 forms a fused ring with a substituent of an adjacent carbon atom.

Clause 8: The compound of clause 1, wherein the compound is represented by Formula (III)-B,

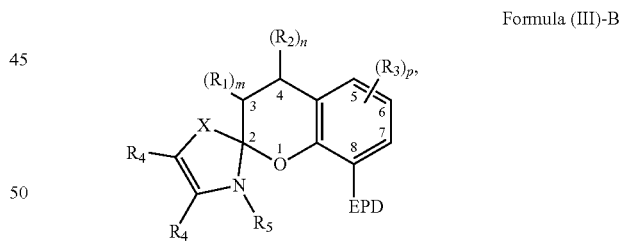

Formula (III)-B wherein, EPD represents a group comprising an electron pair donor atom;
$R_1$ and $R_2$ each independently comprise a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, a spirocyclic group, or any combination thereof, or $R_1$ and $R_2$ together form a cycloalkyl group or a heterocyclic group;
each $R_3$ independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof;

each $R_4$ is a hydrogen, or each $R_4$ together forms a fused aryl ring;

$R_5$ is a hydrogen or alkyl group;

X is $C(Me)_2$, O, N—$R_5$, or S in which Me is a methyl group; m and n are each independently a number selected from 0 to 2; and p is a number selected from 0 to 3.

Clause 9: The compound of clause 8, wherein X is $C(Me)_2$.

Clause 10: The compound of any of clauses 1 to 9, wherein m and n are each 0 or wherein m=0 and n=1 and $R_2$ comprises an alkenyl group.

Clause 11: The compound of clauses 8, 9, or 10, wherein $R_2$ comprises an alkenyl group substituted with two substituents that are the same as B and B' and n is 1.

Clause 12: A chelate comprising the reaction product of the compound of any of clauses 1-10 and a metal compound.

Clause 13: The chelate of clause 12, wherein the metal compound comprises a metal halide, a metal carboxylate, a metal alkoxide, a metal triflate, a metal sulfonate, a metal phosphonate, a metal acetylacetonate, a metal sulfide, a metal oxide, a metal mercaptide, a metal thioglycolate, a metal hydride, or a combination thereof, preferably a metal halide such as a metal chloride, including organometallic metal halides, or a metal carboxylate such as acetate and 2-ethylhexanoate, including organometallic acetates, or a combination thereof.

Clause 14: The chelate of clause 12, wherein the metal compound comprises a tin compound, a zinc compound, a zirconium compound, a titanium compound, a bismuth compound, an iron compound, a copper compound, a lead compound, an aluminum compound, or a combination thereof, preferably a tin compound including alkyltin compounds, a zinc compound, a zirconium compound, an iron compound, or a combination thereof.

Clause 15: The chelate of clause 12, wherein the metal compound comprises dibutyltin dichloride, a bismuth carboxylate, zinc 2-ethylhexanoate, iron(III) chloride, bibutyltin diacetate, zinc chloride, and zirconium tetrachloride Clause 16 A composition comprising: a). a reactive material comprising at least one of: i). one or more cationic polymerizable components; and ii). an active hydrogen functional first component, and a second component reactive with the active hydrogen groups of the first component; and b). a latent catalyst comprising a reaction product formed from components comprising: i. a ligand derived from a compound comprising a chemical structure represented by Formula (I)-B,

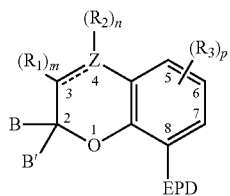

Formula (I)-B wherein, EPD represents a group comprising an electron pair donor atom;

Z comprises carbon or nitrogen;

B and B' are each independently an aryl group, a heteroaryl group, an alkenyl group, or alkynyl group, or B and B' taken together form a spirocyclic group;

$R_1$ and $R_2$ each independently comprise a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, a spirocyclic group, or any combination thereof, or $R_1$ and $R_2$ together form a cycloalkyl group, a heterocyclic group, an aromatic, or a heteroaromatic group;

a bond between positions 3 and 4 is a single bond or a double bond, with the proviso that Z is carbon when the bond between positions 3 and 4 is a single bond; and m and n are each independently a number selected from 0 to 2; and ii. a metal compound sufficient to catalyze the reactive material.

Clause 17: The composition of clause 16, wherein the reactive material comprises one or more cationic polymerizable components.

Clause 18: The composition of clauses 16 or 17, wherein the one or more cationic polymerizable components comprise vinyl compounds, cyclic ether compounds, cyclic thioether compounds, cyclic amine compounds, or combinations thereof.

Clause 19: The composition of any of clauses 16-18, wherein the reactive material comprises the active hydrogen functional first component and the second component reactive with the active hydrogen groups of the first component.

Clause 20: The composition of clause 19, wherein the active hydrogen functional first component comprises one or more hydroxyl groups, thiol groups, amine groups, carboxylic acid groups, carboxamide groups, or combinations thereof.

Clause 21: The composition of clause 20, wherein the active hydrogen functional first component comprises at least two hydroxyl groups, thiol groups, amine groups, carboxylic acid groups, carboxamide groups, or combinations thereof.

Clause 22: The composition of clauses 20 or 21, wherein the second component reactive with the active hydrogen groups of the first component comprises one or more, preferably two, isocyanate groups, isothiocyanate groups, alkoxysilane groups, activated double bonds, epoxide groups, episulfide groups, aziridine groups, or combinations thereof.

Clause 23: The composition of clause 22, wherein the second component reactive with the active hydrogen groups of the first component comprises at least two isocyanate groups, isothiocyanate groups, alkoxysilane groups, activated double bonds, or combinations thereof.

Clause 24: The composition of clause 16, wherein the active hydrogen functional first component comprises one or more, preferably two, hydrazide groups, amine groups, or combinations thereof.

Clause 25: The composition of clause 24, wherein the second component reactive with the active hydrogen groups of the first component comprises one or more, preferably two, ketone groups, aldehyde groups, or combinations thereof.

Clause 26: The composition of any of clauses 16-25, wherein the electron pair donor atom comprises a nitrogen atom, an oxygen atom, a phosphorus atom, or a carbene, preferably a nitrogen atom.

Clause 27: The composition of any of clauses 16-26, wherein the EPD of Formula (I)-B comprises a cyclic ring comprising at least one of a nitrogen atom, an oxygen atom, and/or a phosphorus atom, preferably a nitrogen atom.

Clause 28: The composition of any of clauses 16-27, wherein $R_1$ and $R_2$ each independently comprise an alkyl group, an aryl group, a halo group, an alkenyl group, or an alkynyl group.

Clause 29: The composition of any of clauses 16-28, wherein B and B' taken together form a spirocyclic group comprising a nitrogen, an oxygen, or a sulfur atom, preferably a nitrogen atom.

Clause 30: The composition of any of clauses 16-29, wherein the bond between positions 3 and 4 is a single bond and Z is a carbon.

Clause 31: The composition of any of clauses 16-30, wherein the compound comprises at least one chemical structure represented by at least one of Formula (IV), Formula (V), Formula (VI), and Formula (VII):

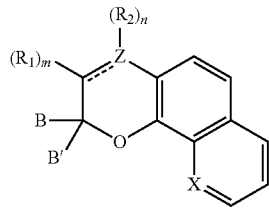

Formula (IV)

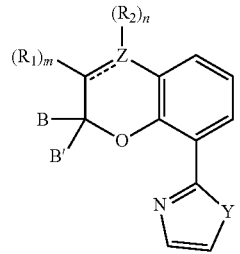

Formula (V)

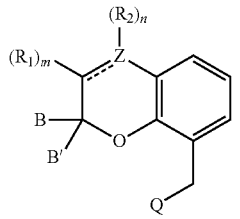

Formula (VI)

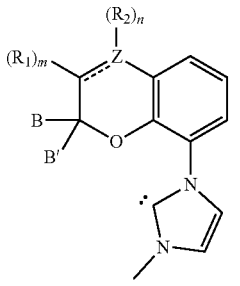

Formula (VII)

wherein, Z comprises carbon or nitrogen;
X is nitrogen or C—OH;
Y is oxygen, sulfur, N—CH$_3$ or —CH=CH—; and
Q comprises an amine or a phosphine.

Clause 32: The composition of any of clauses 16-31, wherein a substituent of each carbon atom located at positions 5-7 independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof.

Clause 33: The composition of any of clauses 16-31, wherein a substituent of a carbon atom at one of positions 5-7 forms a fused ring with a substituent of an adjacent carbon atom.

Clause 34: The composition of any of clauses 16-25, wherein the compound is represented by Formula (III)-B,

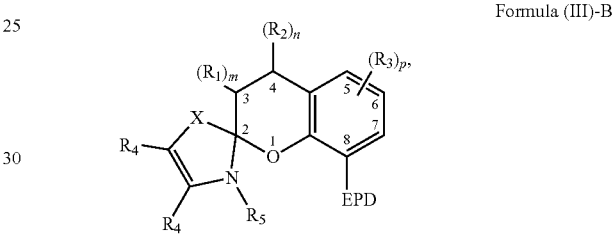

Formula (III)-B wherein, EPD represents a group comprising an electron pair donor atom; $R_1$ and $R_2$ each independently comprise a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, a spirocyclic group, or any combination thereof, or $R_1$ and $R_2$ together form a cycloalkyl group or a heterocyclic group;
each $R_3$ independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof;
each $R_4$ is a hydrogen, or each $R_4$ together forms a fused aryl ring;
$R_5$ is a hydrogen or alkyl group;
X is C(Me)$_2$, O, N—$R_5$, or S in which Me is a methyl group;
m and n are each independently a number selected from 0 to 2; and
p is a number selected from 0 to 3.

Clause 35: The composition of clause 34, wherein X is C(Me)$_2$.

Clause 36: The compound of any of clauses 34 or 35, wherein m and n are each 0 or wherein m=0 and n=1 and $R_2$ comprises an alkenyl group.

Clause 37: The composition of clauses 34, 35, or 36, wherein $R_2$ comprises an alkenyl group substituted with two substituents that are the same as B and B' and n is 1.

Clause 38: The composition of any of clauses 16-37, wherein the metal compound comprises a metal halide, a metal carboxylate, a metal alkoxide, a metal triflate, a metal sulfonate, a metal phosphonate, a metal acetylacetonate, a metal sulfide, a metal oxide, a metal mercaptide, a metal thioglycolate, a metal hydride, or a combination thereof, preferably a metal halide such as a metal chloride, including organometallic metal halides, or a metal carboxylate such as acetate and 2-ethylhexanoate, including organometallic acetates, or a combination thereof.

Clause 39: The composition of any of clauses 16-37, wherein the metal compound comprises a tin compound, a zinc compound, a zirconium compound, a titanium compound, a bismuth compound, an iron compound, a copper compound, a lead compound, an aluminum compound, or a combination thereof, preferably a tin compound including alkyltin compounds, a zinc compound, a zirconium compound, an iron compound, or a combination thereof, preferably a tin compound including alkyltin compounds, a zinc compound, a zirconium compound, an iron compound, or a combination thereof.

Clause 40: The composition of any of clauses 16-37, wherein the metal compound comprises dibutyltin dichloride, a bismuth carboxylate, zinc 2-ethylhexanoate, iron(III) chloride, bibutyltin diacetate, zinc chloride, and zirconium tetrachloride Clause 41: A substrate coated with a coating formed from the composition of any of clauses 16-40.

Clause 42: An article formed from the composition of any of clauses 16-40.

Clause 43: A polymeric sheet formed from the composition of any of clauses 16-40.

Clause 44: A method of catalyzing a reaction comprising irradiating a composition as defined in any of clauses 16-40.

Clause 45: The method of clause 44, further comprising applying the composition to at least a portion of a surface of a substrate or to an interior portion of a mold prior to irradiating the composition.

Clause 46: The method of clause 44, further comprising applying the composition to at least a portion of a surface of a substrate or to an interior portion of a mold during or after irradiating the composition.

Clause 47: The method of any of clauses 44-46, wherein the composition is irradiated with visible light.

Clause 48: The use of a chelate as defined in any of clauses 12-15 as a latent catalyst in a polymerization reaction.

Clause 49: The use of a composition as defined in any of clauses 16-40 involving irradiation with actinic radiation such that the ligand is disassociated from the reaction product.

Whereas particular embodiments of this invention have been described above for purposes of illustration, it will be evident to those skilled in the art that numerous variations of the details of the present invention may be made without departing from the invention as defined in the appended claims.

The invention claimed is:

1. A compound comprising a chemical structure represented by Formula (II)-B that can coordinate with a metal,

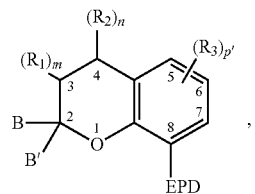

Formula (II)-B wherein, EPD represents a group comprising an electron pair donor atom;

B and B' are each independently an aryl group, a heteroaryl group, an alkenyl group, or alkynyl group, or B and B' taken together form a spirocyclic group comprising a nitrogen or a sulfur atom directly bonded to the 2-position;

$R_1$ and $R_2$ each independently comprise a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, a spirocyclic group, or any combination thereof, or $R_1$ and $R_2$ together form a cycloalkyl group or a heterocyclic group; and each $R_3$ independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof;

m and n are each independently a number selected from 0 to 2; and p is a number selected from 0 to 3.

2. The compound of claim 1, wherein the EPD of Formula (II)-B comprises a nitrogen atom, an oxygen atom, a phosphorus atom, a carbene or a cyclic ring comprising at least one of a nitrogen atom, an oxygen atom, and/or a phosphorus atom.

3. The compound of claim 1, wherein a substituent of each carbon atom located at positions 5-7 independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof or where a substituent of a carbon atom at one of positions 5-7 forms a fused ring with a substituent of an adjacent carbon atom.

4. The compound of claim 1, wherein the compound is represented by Formula (III)-B,

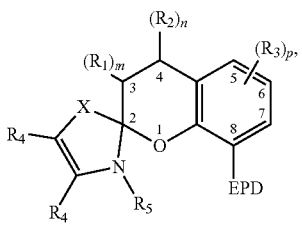

Formula (III)-B wherein, EPD represents a group comprising an electron pair donor atom;

$R_1$ and $R_2$ each independently comprise a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, a spirocyclic group, or any combination thereof, or Ri and R2 together form a cycloalkyl group or a heterocyclic group;

each $R_3$ independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof;

each $R_4$ is a hydrogen, or each $R_4$ together forms a fused aryl ring;

$R_5$ is a hydrogen or alkyl group;

X is $C(Me)_2$, O, N—$R_5$, or S in which Me is a methyl group;

m and n are each independently a number selected from 0 to 2; and p is a number selected from 0 to 3.

5. The compound of claim 4, wherein $R_2$ comprises an alkenyl group substituted with two substituents that are the same as B and B' and n is 1.

6. A composition comprising:
a). a reactive material comprising at least one of:
i). one or more cationic polymerizable components; and
ii). an active hydrogen functional first component, and a second component reactive with the active hydrogen groups of the first component to form a polymer; and
b). a latent catalyst comprising a reaction product formed from components comprising:
i. a ligand derived from a compound comprising a chemical structure represented by Formula (1)-B,

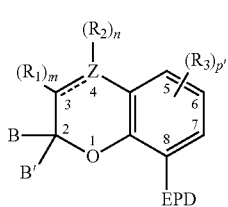

Formula (I)-B wherein, EPD represents a group comprising an electron pair donor atom;

Z comprises carbon or nitrogen;

B and B' are each independently an aryl group, a heteroaryl group, an alkenyl group, or alkynyl group, or B and B' taken together form a spirocyclic group comprising a nitrogen or a sulfur atom directly bonded to the 2-position;

$R_1$ and $R_2$ each independently comprise a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, a spirocyclic group, or any combination thereof, or Ri and R2 together form a cycloalkyl group, a heterocyclic group, an aromatic, or a heteroaromatic group;

each $R_3$ independently comprises a hydroxyl group, an alkyl group, an aryl group, a haloalkyl group, an alkoxy group, an amino group, a nitrogen-containing heterocycle group, an alkylthio group, an arythio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof:

a bond between positions 3 and 4 is a single bond or a double bond, with the proviso that Z is carbon when the bond between positions 3 and 4 is a single bond; and m and n are each independently a number selected from 0 to 2;

p is a number selected from 0 to 3; and ii. a metal compound sufficient to catalyze the reaction of the reactive material.

7. The composition of claim 6, wherein the reactive material comprises the active hydrogen functional first component and the second component reactive with the active hydrogen groups of the first component.

8. The composition of claim 7, wherein the active hydrogen functional first component comprises one or more hydroxyl groups, thiol groups, amine groups, carboxylic acid groups, carboxamide groups, or combinations thereof.

9. The composition of claim 7, wherein the second component reactive with the active hydrogen groups of the first component comprises one or more isocyanate groups, isothiocyanate groups, alkoxysilane groups, activated double bonds, epoxide groups, episulfide groups, aziridine groups, or combinations thereof.

10. The composition of claim 7, wherein the active hydrogen functional first component comprises one or more hydrazide groups, amine groups, or combinations thereof, and wherein the second component reactive with the active hydrogen groups of the first component comprises one or more ketone groups, aldehyde groups, or combinations thereof.

11. The composition of claim 6, wherein the EPD of Formula (I)-B comprises a nitrogen atom, an oxygen atom, a phosphorus atom, a carbene or a cyclic ring comprising at least one of a nitrogen atom, an oxygen atom, and/or a phosphorus atom.

12. The composition of claim 6, wherein the compound comprises at least one chemical structure represented by at least one of Formula (IV), Formula (V), Formula (VI), and Formula (VII):

Formula (IV)

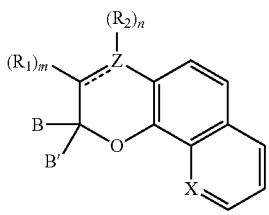

Formula (V)

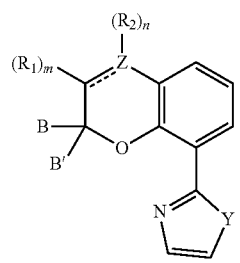

Formula (VI)

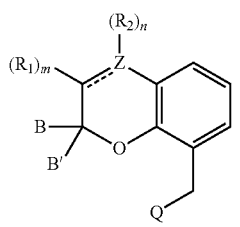

Formula (VII)

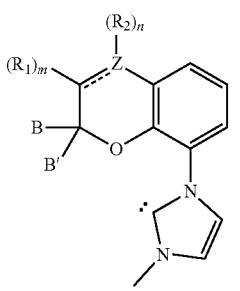

wherein, Z comprises carbon or nitrogen;
X is nitrogen or C—OH;
Y is oxygen, sulfur, N—CH$_3$ or —CH═CH—; and
Q comprises an amine or a phosphine.

13. The composition of claim 6, wherein a substituent of each carbon atom located at positions 5-7 independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof or where a substituent of a carbon atom at one of positions 5-7 forms a fused ring with a substituent of an adjacent carbon atom.

14. The composition of claim 6, wherein the compound is represented by Formula (III)-B, Formula (III)-B

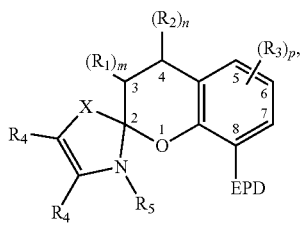

wherein, EPD represents a group comprising an electron pair donor atom;
R$_1$ and R$_2$ each independently comprise a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, a spirocyclic group, or any combination thereof, or R$_1$ and R$_2$ together form a cycloalkyl group or a heterocyclic group;
each R$_3$ independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof;
each R$_4$ is a hydrogen, or each R$_4$ together forms a fused aryl ring;
R$_5$ is a hydrogen or alkyl group;
X is C(Me)$_2$, O, N—R$_5$, or S in which Me is a methyl group;
m and n are each independently a number selected from 0 to 2; and
p is a number selected from 0 to 3.

15. The composition of claim 14, wherein R$_2$ comprises an alkenyl group substituted with two substituents that are the same as B and B' and n is 1.

16. The composition of claim 6, wherein the metal compound comprises a metal halide, a metal carboxylate, a metal alkoxide, a metal triflate, a metal sulfonate, a metal phosphonate, a metal acetylacetonate, a metal sulfide, a metal oxide, a metal mercaptide, a metal thioglycolate, a metal hydride, or a combination thereof.

17. The composition of claim 6, wherein the metal compound comprises a tin compound, a zinc compound, a zirconium compound, a titanium compound, a bismuth compound, an iron compound, a copper compound, or a combination thereof.

18. A substrate coated with a coating formed from the composition of claim 6.

19. An article formed from the composition of claim 6.

20. A method of catalyzing a reaction comprising irradiating a composition comprising:
  a). a reactive material comprising at least one of:
    i). one or more cationic polymerizable components; and
    ii). an active hydrogen functional first component, and a second component reactive with the active hydrogen groups of the first component; and b). a latent catalyst comprising a reaction product formed from components comprising:
  i. a ligand derived from a compound represented by Formula (1)-B,

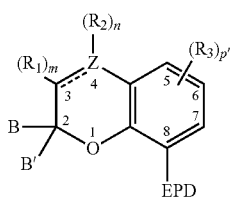

Formula (I)-B wherein, EPD represents a group comprising an electron pair donor atom;

Z comprises carbon or nitrogen;

B and B' are each independently an aryl group, a heteroaryl group, an alkenyl group, or alkynyl group, or B and B' taken together form a spirocyclic group;

$R_1$ and $R_2$ each independently comprise a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, a spirocyclic group, or any combination thereof, or $R_1$ and $R_2$ together form a cycloalkyl group, a heterocyclic group, an aromatic, or a heteroaromatic group;

each $R_3$ independently comprises a hydroxyl group, an alkyl group, an aryl group, a haloalkyl group, an alkoxy group, an amino group, a nitrogen-containing heterocycle group, an alkylthio group, an arylthio group, an aryloxy group, an aralkyl, a nitrile group, a nitro group, a formyl group, a carboxylic acid group, a ketone group, an ester group, a carboxylate group, a halo group, a group comprising a siloxane, an alkenyl group, an alkynyl group, or any combination thereof;

a bond between positions 3 and 4 is a single bond or a double bond, with the proviso that Z is carbon when the bond between positions 3 and 4 is a single bond; and m and n are each independently a number selected from 0 to 2 p is a number selected from o to 3; and ii. a metal compound sufficient to catalyze the reactive material, wherein the composition is irradiated with actinic radiation such that the ligand is disassociated from the reaction product.

* * * * *